United States Patent [19]

Boroschewski et al.

[11] 4,229,208
[45] Oct. 21, 1980

[54] DIURETHANES WITH SELECTIVE HERBICIDAL ACTION

[75] Inventors: Gerhard Boroschewski; Friedrich Arndt, both of Berlin, Fed. Rep. of Germany

[73] Assignee: Schering AG, Berlin and Bergkamen, Fed. Rep. of Germany

[21] Appl. No.: 557,286

[22] Filed: Mar. 11, 1975

[30] Foreign Application Priority Data

Mar. 20, 1974 [DE] Fed. Rep. of Germany ....... 2413933

[51] Int. Cl.³ .............................................. A01N 9/20
[52] U.S. Cl. ......................................... 71/111; 560/29
[58] Field of Search ............... 260/471 C, 472; 71/111

[56] References Cited

U.S. PATENT DOCUMENTS

| 3,404,975 | 10/1968 | Wilson et al. | 260/471 C X |
| 3,692,820 | 9/1972 | Boroschewski et al. | 260/472 |
| 3,865,867 | 2/1975 | Olin et al. | 260/472 |
| 3,898,075 | 5/1975 | Freund et al. | 71/111 |
| 3,901,936 | 8/1975 | Boroschewski | 260/471 C |

FOREIGN PATENT DOCUMENTS 1567151  7/1969 Fed. Rep. of Germany ....... 260/471 C

Primary Examiner—Richard Raymond
Attorney, Agent, or Firm—Michael J. Striker

[57] ABSTRACT

Diurethanes of the general formula

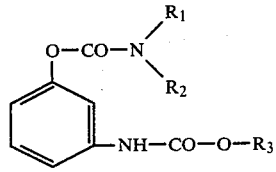

wherein
R₁ is allyl or a C₁ to C₄ alkyl radical possibly substituted by halogen;
R₂ is a C₁ to C₄ alkyl radical possibly substituted by halogen, a C₃ to C₄ alkenyl or alkinyl radical, cyclohexyl, phenyl, C₁ to C₃ alkylphenyl, C₁ to C₃ alkoxyphenyl, halogen phenyl, benzyl or phenylethyl;
R₃ is a C₃ or C₄ hydrocarbon radical possibly substituted by halogen, or halogen ethyl; or
R₁ is ethyl or allyl, R₂ is phenyl, C₁ to C₃ alkylphenyl, C₁ to C₃ alkoxyphenyl or halogen phenyl, and R₃ is methyl or ethyl;

are provided as herbicidal agents notably in cotton cultivation in the pre-emergent and emergent stages of development of such cotton; including other cultivations such as for cereal, corn and soybean.

1 Claim, No Drawings

DIURETHANES WITH SELECTIVE HERBICIDAL ACTION

The invention concerns new diurethanes with selective herbicidal action in particular in cotton cultivations.

The selective control of weeds in cultivated plants is always especially difficult when the biologic relationship between crop plant and weed is very close and, for example, they belong to the same plant family. It is the rule, therefore, that selective herbicides, in particular those which act via the aboveground plant parts (leaf herbicides) present corresponding action gaps. Thus, in cotton, which botanic-systemically belongs to the family of the Malvaceae, malvaceous weeds, namely Sida spinosa and Abutilon theophrastic, have spread widely in recent years. These are seed weeds which germinate together with the cotton and reach growth heights of 0.2–1 m and 0.6–1.2 m, respectively. When occurring en masse, they can practically choke the cotton cultivation. The known selective herbicides in cotton, as for example N-(3-trifluoromethylphenyl)-N',N'-dimethyl urea (see U.S. Pat. No. 3,134,665) can be applied only as pre-seeding and pre-emergence herbicides or can develop sufficient tolerance for cotton and sufficient herbicidal action against a number of weeds only in this manner of application. Instead, they exert remarkably little activity in the control of the mentioned problem weeds Sida spinosa and Abutilon theophrastic, owing to which conditions arise which contribute to the further spread and propagation of these weeds. The herbicidal action of selective biscarbamates, e.g. of 3-methoxycarbonylaminophenyl-N-(3-methylphenyl) carbamate, is already known (German Pat. No. 1,567,151). A sufficient selectivity for cotton and an action against problem weeds, like Sida spinosa and Abutilon theophrasti, has not been demonstrated for these herbicides until now.

It is an object of the present invention to provide a herbicidal agent which overcomes the disadvantages of the known agents and can be used more successfully even in post-emergence selectively against weeds difficult to control until now, in particular in cotton, and moreover also in cereal, corn, and soybean cultivations.

This problem is solved according to the invention by an agent which is characterized by a content of at least one compound of the general formula

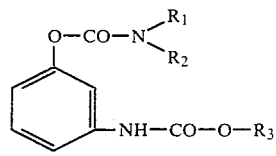

wherein
- $R_1$ is allyl or a $C_1$ to $C_4$ alkyl radical possibly substituted by halogen;
- $R_2$ is a $C_1$ to $C_4$ alkyl radical possibly substituted by halogen, a $C_3$ to $C_4$ alkenyl or alkinyl radical, cyclohexyl, phenyl, $C_1$ to $C_3$ alkylphenyl, $C_1$ to $C_3$ alkoxyphenyl, halogen phenyl, benzyl or phenylethyl;
- $R_3$ is a $C_3$ or $C_4$ hydrocarbon radical possibly substituted by halogen, or halogen ethyl, or $R_1$ is ethyl or allyl, $R_2$ is phenyl, $C_1$ to $C_3$ alkylphenyl, $C_1$ to $C_3$ alkoxyphenyl or halogen phenyl, and $R_3$ is methyl or ethyl.

The designation $C_1$ to $C_3$ or $C_4$ alkyl comprises, for example, the radicals methyl, ethyl, propyl, isopropyl, n-butyl, isobutyl, sec.-butyl, tert.-butyl. The designation $C_1$ to $C_3$ alkoxyphenyl comprises on the other hand, for example, the radicals methoxyphenyl and ethoxyphenyl.

The agents of the invention excel by a surprisingly good tolerance to cotton. Besides their use with respect to cotton, the agents can be used for weed control in cereals, corn and soybeans.

The agents of the invention are most effective when used in the post-emergence stage. The agents of the invention have a wide spectrum of action. Furthermore, the herbicidal effect extends to many species of weeds. The volumes of application for selective weed control are about 0.5 to 5 kg active substance per hectare. Expediently, the active substances of the invention are used in the form of preparations, such as powders, scatters, granulates, solutions, emulsions or suspensions, with the addition of liquid and/or solid vehicles or diluents and also, if needed, wetting, adhesive, emulsifying, and/or dispersing aids.

Suitable liquid vehicles are water, aliphatic or aromatic hydrocarbons, such as benzene, toluene, xylene, cyclohexanone, isophorone, also mineral oil fractions.

As solid vehicles that may be used are suitable mineral earths, such as silicious clay, silica gel, talc, kaolin, attaclay, limestone, silicic acid and plant products, e.g. flours.

Among surface active substances that may be used are calcium lignin sulfonate, polyoxyethylene-octyl-phenol ether, naphthalene sulfonic acids, phenol sulfonic acids, formaldehyde condensates, fatty alcohol sulfates, and fatty acid alkali and alkaline earth salts.

It has been found, surprisingly, that the herbicidal action and the selectivity of the agents can be increased when they contain the surface-active substances in proportions exceeding the usual quantities.

The proportion of the active substance or substances in the various preparations may vary within wide limits. As an example, the agents contain about 20 to 80 percent by weight of active substances, about 80 to 20 percent by weight of liquid or solid vehicles, and possibly up to 30 percent by weight of surface-active substances.

The application of the agents can take place in the usual manner with water as vehicle in spray solution quantities of 100 to 1000 liters/ha. For total weed control, necessary spray solution quantities of more than 1000 liters/ha may be applied. Application of the agents in so-called "ultra-low volume" is possible, as is also their application in the form of so-called micro-granulates.

The production of these preparations is carried out in a manner known in the art, such as by mixing or grinding methods. If desired, the individual components may be mixed shortly before their use, as is done in the practice of so-called tank mixing.

The new compounds of the invention can be produced by methods known in themselves, e.g. by reacting (a) compounds of the general formula

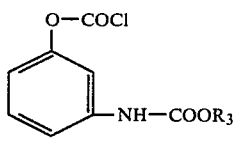

with an amine of the general formula

in the presence of an acid acceptor, such as with the addition of excess amine, or of an inorganic base, as for example caustic soda, sodium carbonate, potassium carbonate, or a tertiary organic base, such as triethylamine, or by reacting (b) compounds of the general formula

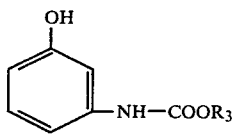

in the presence of a tertiary organic base, as for example triethylamine or pyridine or as alkali salts with carbamoyl chlorides of the general formula

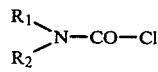

at temperatures of 0°–100° C., or by catalytically hydrating (c) compounds of the general formula

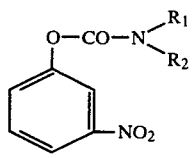

e.g. with the use of nickel in methanol to the corresponding amine and subsequently reacting with compounds of the general formula Cl-COOR₃      II in the presence of an acid acceptor, of an inorganic base, such as caustic soda, sodium carbonate or potassium carbonate, or a tertiary organic base, such as triethylamine, to the desired process products and then isolating the latter in the usual manner. It is to be noted that $R_1$, $R_2$ and $R_3$ in the above have the same meaning as in formula I.

The following examples will explain the production of the compounds to be used according to the invention.

1. n-Propyl-N-(3-(N,N-di-sec.-butylcarbamoyloxy)-phenyl)-carbamate (Compound #1)

The sodium salt produced from 19.5 g (0.1 mole) of 3-hydroxycarbanilic acid-n-propyl ester and sodium methylate (from 2.3 g of sodium) in absolute methanol is suspended in 100 ml of dry methyl isobutyl ketone after thorough removal of the methanol under vacuum. Under agitation, a solution of 19.1 g (0.1 mole) di-sec.-butylcarbamoyl chloride in 50 ml methyl isobutylketone is added in drops, the temperature rising to about 30° C. Then agitation is continued for one hour at 70° C. After cooling, admix with about 200 ml acetic ester and wash at 0° C. with dilute caustic soda and water, dry with magnesium sulfate, and evaporate under reduced pressure.

The yield: 30.6 g = 87% of the theory.
$n_D^{20} = 1.4925$.

2. Isopropyl-N-(3-(N-ethyl-N-(2-chloroethyl)-carbamoyloxy-phenyl) carbamate (Compound #2)

A solution of 14.4 g (0.1 mole) N-ethyl-N-(2-chloroethyl)-amine hydrochloride in 50 ml water is admixed with 30 ml acetic ester. While stirring and cooling to 10° to 15° C., a solution of 25.8 g (0.1 mole) chloroformic acid-3-(N-isopropoxycarbonylamino)-phenyl ester in 50 ml acetic ester and simultaneously a solution of 27.6 g (0.2 mole) potassium carbonate in 50 ml water is added in drops. Agitation is continued for 30 minutes at 15° C. Then the organic phase is separated, diluted with about 50 ml acetic ester and washed at 0° C. with a little dilute caustic soda, dilute hydrochloric acid and water. After drying with magnesium sulfate, concentrate under reduced pressure. Upon addition of pentane, the reaction product crystallizes out. It is suction filtered and washed with ether-pentane.

The yield: 22.4 g = 68% of the theory.
M.p. 105°–107° C.

The following compounds can be produced in an analogous manner.

| Compound No. | Name of Compound | Physical Constants |
|---|---|---|
| 3 | Isopropyl-N-(3-(N-methyl-N-(1-methyl) propinyl)-carbamoyloxy)-phenyl)carbamate | m.p. 68–70° C. |
| 4 | Isopropyl-N-(3-N-methyl-N-(2-chlorethyl)-carbamoyloxy)-phenyl)-carbamate | m.p. 98–99° C. |
| 5 | Ethyl-N-(3-(N-allyl-N-phenylcarbamoyl-oxy)-phenyl)-carbamate | m.p. 93–95° C. |
| 6 | Ethyl-N-(3-(N-allyl-N-(2-methylphenyl)-carbamoyloxy)-phenyl)-carbamate | m.p. 72–76° C. |
| 7 | Isopropyl-N-(3-(N,N-diallylcarbamoyl-oxy)-phenyl)-carbamate | m.p. 70–71° C. |
| 8 | Isopropyl-N-(3-N-ethyl-N-isopropyl-carbamoyloxy)-phenyl)-carbamate | m.p. 123–124° C. |
| 9 | Isopropyl-N-(3-(N-butyl-N-ethylcarbamoyloxy)-phenyl)-carbamate | $n_D^{20}$: 1.5101 |
| 10 | Isopropyl-N-(3-N,N-diisopropyl-carbamoyloxy)-phenyl)-carbamate | m.p. 138–139° C. |
| 11 | Isopropyl-N-(3-N-butyl-N-phenylcarba- | |

-continued

| Compound No. | Name of Compound | Physical Constants |
|---|---|---|
| | moyloxy)-phenyl)-carbamate | m.p. 98–99° C. |
| 12 | Ethyl-N-(3-(N-ethyl-N-phenylcarbamoyloxy)-phenyl)-carbamate | m.p. 145–146° C. |
| 13 | Isopropyl-N-(3-(N-ethyl-N-phenylcarbamoyloxy)-phenyl)-carbamate | m.p. 94–95° C. |
| 14 | Isopropyl-N-(3-(N-cyclohexyl-N-methylcarbamoyloxy)-phenyl-carbamate | m.p. 114–115° C. |
| 15 | Isopropyl-N-(3-N-allyl-N-phenyl-carbamoyloxy)-phenyl)-carbamate | m.p. 65–66° C. |
| 16 | Isopropyl-N-(3-(N-methyl-N-phenyl-carbamoyloxy)-phenyl)-carbamate | m.p. 90–91° C. |
| 17 | Isopropyl-N-(3-(N-cyclohexyl-N-isobutylcarbamoyloxy)-phenyl)-carbamate | m.p. 124–125° C. |
| 18 | Isopropyl-N-(3-(N-cyclohexyl-N-propylcarbamoyloxy)-phenyl)-carbamate | m.p. 104–105° C. |
| 19 | Isopropyl-N-(3-(N-cyclohexyl-N-isopropylcarbamoyloxy)-phenyl)-carbamate | m.p. 103–104° C. |
| 20 | Isopropyl-N-(3-(N-butyl-N-cyclohexyl-carbamoyloxy)-phenyl)-carbamate | m.p. 115–116° C. |
| 21 | Isopropyl-N-(3-(N-methyl-N-phenethyl-carbamoyloxy)-phenyl)-carbamate | m.p. 97–98° C. |
| 22 | Isopropyl-N-(3-(N-benzyl-N-Methyl-carbamoyloxy)-phenyl)-carbamate | m.p. 95–96° C. |
| 23 | Isopropyl-N-(3-(N-ethyl-N-benzyl-carbamoyloxy)-phenyl)-carbamate | $n_D^{20} = 1.5375$ |
| 24 | Isopropyl-N-(3-(N,N-bis-(2-chlor-ethyl)-carbamoyloxy)-phenyl)-carbamate | $n_D^{20} = 1.5260$ |
| 25 | Isopropyl-N-(3-(N-sec.-butyl-N-cyclohexyl-carbamoyloxy)-phenyl)-carbamate | m.p. 122–124° C. |
| 26 | sec.-butyl-N-(3-(N-ethyl-N-phenyl-carbamoyloxy)-phenyl)-carbamate | m.p. 91° C. |
| 27 | 3-Chlorpropyl-N-(3-(N-ethyl-N-phenyl-carbamoyloxy)-phenyl)-carbamate | m.p. 85° C. |
| 28 | 2-Chloro-1-methylethyl-N-(3-(N-ethyl-N-phenylcarbamoyloxy)-phenyl)-carbamate | m.p. 85° C. |
| 29 | 2-Chloro-1-methylethyl-N-(3-(N-butyl-N-phenylcarbamoyloxy)-phenyl)-carbamate | m.p. 101° C. |
| 30 | 3-Chlorpropyl-N-(3-(N,N-bis-(2-chloroethyl)-carbamoyloxy)-phenyl)-carbamate | m.p. 65° C. |
| 31 | 2-Chloroethyl-N-(3-(N,N-bis-(2-chloroethyl)-carbamoyloxy)-phenyl)-carbamate | m.p. 72° C. |
| 32 | sec.-Butyl-N-(3-(N,N-bis-(2-chloroethyl)-carbamoyloxy)-phenyl-carbamate | $n_D^{20} = 1.5300$ |
| 33 | 2-Chloroethyl-N-(3-(N-ethyl-N-phenyl-carbamoyloxy)-phenyl)-carbamate | m.p. 110° C. |
| 34 | 2-Chloro-1-methylethyl-N-(N,N-bis-(2-chloroethyl)-carbamoyloxy)-phenyl)-carbamate | m.p. 71° C. |
| 35 | n-Propyl-N-(3-(N-butyl-N-phenylcarbamoyloxy)-phenyl)-carbamate | $n_D^{20} = 1.5380$ |
| 36 | n-Propyl-N-(3-(N,N bis-(2-chloroethyl)-carbamoyloxy)-phenyl)-carbamate | m.p. 49–51° C. |
| 37 | Ethyl-N-(3-(N-ethyl-N-(4-methylphenyl)-carbamoyloxy)-phenyl)-carbamate | m.p. 87–88° C. |
| 38 | Ethyl-N-(3-(N-ethyl-N-(3-methylphenyl)-carbamoyloxy)-phenyl-carbamate | m.p. 79–80° C. |
| 39 | Ethyl-N-(3-(N-ethyl-N-(2-methylphenyl)-carbamoyloxy)-phenyl)-carbamate | m.p. 117–118° C. |
| 40 | Isopropyl-N-(3-(N-ethyl-N-(3-methyl-phenyl)-carbamoyloxy)-phenyl)-carbamate | m.p. 119–120° C. |
| 41 | Isopropyl-N-(3-(N-ethyl-N-(2-methyl-phenyl)-carbamoyloxy)-phenyl)-carbamate | m.p. 117–118° C. |
| 42 | Isopropyl-N-(3-(N-methyl-N-(3-methyl-phenyl)-carbamoyloxy)-phenyl)-carbamate | m.p. 81–82° C. |
| 43 | Isopropyl-N-(3-(N-methyl-N-(4-methyl-phenyl)-carbamoyloxy)-phenyl)-carbamate | $n_D^{20} = 1.5466$ |
| 44 | Isopropyl-N-(3-(N-methyl-N-(2-methyl-phenyl)-carbamoyloxy)-phenyl)-carbamate | m.p. 122–124° C. |
| 45 | Isopropyl-N-(3-(N-ethyl-N-(4-methyl-phenyl)-carbamoyloxy)-phenyl)-carbamate | m.p. 58–60° C. |
| 46 | n-Propyl-N-(3-(N-ethyl-N-phenyl-carbamoyloxy)-phenyl)-carbamate | m.p. 104° C. |
| 47 | sec.-Butyl-N-(3-(N-butyl-N-phenyl-carbamoyloxyphenyl)-carbamate | m.p. 77° C. |
| 48 | sec.-Butyl-N-(3-(N-ethyl-N-(2-bromethyl)-carbamoyloxy)-phenyl)-carbamate | m.p. 69–70° C. |
| 49 | Isopropyl-N-(3-(N-ethyl-N-(2-bromoethyl)-carbamoyloxy)-phenyl)-carbamate | m.p. 104° C. |
| 50 | 2-Bromoethyl-N-(3-(N-ethyl-N-phenyl- | |

| Compound No. | Name of Compound | Physical Constants |
|---|---|---|
| | carbamoyloxy)-phenyl)-carbamate | m.p. 103° C. |
| 51 | 2-Bromoethyl-N-(3-(N-butyl-N-phenyl-carbamoyloxy)-phenyl)-carbamate | m.p. 84° C. |
| 52 | 2-Bromoethyl-N-(3-(N,N-bis-(2-chloro-ethyl)-carbamoyloxy)-phenyl)-carbamate | m.p. 71–73° C. |
| 53 | 2-Chloroethyl-N-(3-(N-butyl-N-phenyl-carbamoyloxy)-phenyl)-carbamate | m.p. 80–82° C. |
| 54 | 3-Chloropropyl-N-(3-(N-ethyl-N-(2-bromoethyl)-carbamoyloxy)-phenyl)-carbamate | $n_D^{20} = 1.5450$ |
| 55 | 2-Bromoethyl-N-(3-(N-ethyl-N-(2-bromoethyl)-carbamoyloxy)-phenyl)-carbamate | $n_D^{20} = 1.5530$ |
| 56 | sec.-Butyl-N-(3-(N-methyl-N-(1-methylpropinyl)-carbamoyloxy)-phenyl)-carbamate | $n_D^{20} = 1.5046$ |
| 57 | 2-Chloroethyl-N-(3-(N-ethyl-N-(2-bromoethyl)-carbamoyloxy)-phenyl)-carbamate | m.p. 72–73° C. |
| 58 | sec.-Butyl-N-(3-(N,N-dipropylcarbamoyloxy)-phenyl)-carbamate | m.p. 84–85° C. |
| 59 | sec.-Butyl-N-(3-(N-ethyl-N-butylcarbamoyloxy)-phenyl)-carbamate | m.p. 64–65° C. |
| 60 | Propyl-N-(3-(N-methyl-N-phenylcarbamoyloxy)-phenyl)-carbamate | m.p. 100–102° C. |
| 61 | Propyl-N-(3-(N-ethyl-N-(2-methylphenyl)-carbamoyloxy)-phenyl)-carbamate | m.p. 107–109° C. |
| 62 | Propyl-N-(3-(N-ethyl-N-butyl-carbamoyloxy)-phenyl)-carbamate | $n_D^{20} = 1.5166$ |
| 63 | Propyl-N-(3-(N-di-sec.-butylcarbamoyloxy)-phenyl)-carbamate | $n_D^{20} = 1.4925$ |
| 64 | Isopropyl-N-(3-(N-isopropyl-N-(2-chlorethyl)-carbamoyloxy)-phenyl)-carbamate | m.p. 82–86° C. |
| 65 | Isopropyl-N-(3-(tert.-butyl-N-(2-chloroethyl)-carbamoyloxy)-phenyl)-carbamate | m.p. 69–71° C. |
| 66 | Propyl-N-(3-(N-ethyl-N-(3-methylphenyl)-carbamoyloxy)-phenyl)-carbamate | m.p. 116–117° C. |
| 67 | Propyl-N-(3-(N-ethyl-N-(4-methylphenyl)-carbamoyloxy)-phenyl)-carbamate | m.p. 70–71° C. |
| 68 | 3-Chlorpropyl-N-(3-(N-phenyl-N-propyl-carbamoyloxy)-phenyl)-carbamate | m.p. 80° C. |
| 69 | Propyl-N-(3-(N-allyl-N-phenylcarbamoyloxy)-phenyl)-carbamate | m.p. 73–74° C. |
| 70 | Ethyl-N-(3-(N-allyl-N-phenylcarbamoyloxy)-phenyl)-carbamate | m.p. 93–95° C. |
| 71 | Ethyl-N-(3-(N-ethyl-N-phenylcarbamoyloxy)-phenyl)-carbamate | m.p. 145–146° C. |
| 72 | Isopropyl-N-(3-(N-allyl-N-phenyl-carbamoyloxy)-phenyl)-carbamate | m.p. 65–66° C. |
| 73 | Propyl-N-(3-(N-ethyl-N-isopropyl-carbamoyloxy)-phenyl)-carbamate | m.p. 111–112° C. |
| 74 | Isopropyl-N-(3-(N,N-di-isobutylcarbamoyloxy)-phenyl)-carbamate | m.p. 116° C. |
| 75 | sec.-Butyl-N-(3-(N-isobutyl-N-methyl-carbamoyloxy)-phenyl)-carbamate | m.p. 70° C. |
| 76 | 2-Chloroethyl-N-(3-(N-ethyl-N-butyl-carbamoyloxy)-phenyl)-carbamate | $n_D^{20} = 1.5262$ |
| 77 | 2-Chloroethyl-N-(3-(N-methyl-N-phenyl-carbamoyloxy)-phenyl)-carbamate | m.p. 94–95° C. |
| 78 | 2-Chloroethyl-N-(3-N-allyl-N-phenyl-carbamoyloxy)-phenyl)-carbamate | m.p. 89–91° C. |
| 79 | 2-Chloroethyl-N-(3-(N-phenyl-N-isopropyl-carbamoyloxy)-phenyl)-carbamate | m.p. 138–139° C. |
| 80 | 2-Chloroethyl-N-(3-(N,N-dimethyl-carbamoyloxy)-phenyl)-carbamate | m.p. 122–124° C. |
| 81 | 2-Chloroethyl-N-(3-(N,N-diethylcarbamoyloxy)-phenyl)-carbamate | m.p. 92–93° C. |
| 82 | 2-Chloroethyl-N-(3-(N,N-diisobutyl-carbamoyloxy)-phenyl)-carbamate | m.p. 83–85° C. |
| 83 | 2-Bromoethyl-N-(3-(N-methyl-N-phenyl-carbamoyloxy)-phenyl)-carbamate | m.p. 83–84° C. |
| 84 | 2-Bromoethyl-N-(3-(N,N-diethyl-carbamoyloxy)-phenyl)-carbamate | m.p. 96–97° C. |
| 85 | 2-Bromoethyl-N-(3-(N-ethyl-N-(2-methylphenyl)-carbamoyloxy)-phenyl)-carbamate | m.p. 136–137° C. |
| 86 | 2-Bromoethyl-N-(3-(N-isopropyl-N-phenylcarbamoyloxy)-phenyl)-carbamate | m.p. 116–118° C. |

-continued

| Compound No. | Name of Compound | Physical Constants |
|---|---|---|
| 87 | sec.-Butinyl-N-(3-(N-methyl-N-phenyl-carbamoyloxy)-phenyl)-carbamate | m.p. 100–101° C. |
| 88 | sec-Butinyl-N-(3-(N-ethyl-N-phenyl-carbamoyloxy)-phenyl)-carbamate | m.p. 132–133° C. |
| 89 | sec.-Butinyl-N-(3-(N,N-diethyl-carbamoyloxy)-phenyl)-carbamate | m.p. 98–99° C. |
| 90 | sec.-Butinyl-N-(3-(N,N-bis-(2-chloroethyl)-carbamoyloxy)-phenyl)-carbamate | m.p. 95–96° C. |
| 91 | Isopropyl-N-(3-(N,N-bis-(1-chlor-1-methylethyl)-carbamoyloxy)-phenyl)-carbamate | m.p. 92–94° C. |
| 92 | Isopropyl-N-(3-(N-methyl-N-(2-bromoethyl)-carbamoyloxy)-phenyl)-carbamate | m.p. 88–90° C. |
| 93 | sec.-Butyl-N-(3-(N-benzyl-N-methyl-carbamoyloxy)-phenyl)-carbamate | m.p. 85–87° C. |
| 94 | sec.-Butyl-N-(3-(N-ethyl-N-(3-methylphenyl)-carbamoyloxy)-phenyl)-carbamate | m.p. 98–100° C. |
| 95 | sec.-Butyl-N-(3-(N,N-diallyl-carbamoyloxy)-phenyl)-carbamate | m.p. 58–60° C. |
| 96 | sec.-Butyl-N-(3-(N-(2-bromoethyl)-N-tert.-butylcarbamoyloxy-phenyl)-carbamate | m.p. 86–88° C. |
| 97 | Allyl-N-(3-(N-butyl-N-phenyl-carbamoyloxy)-phenyl)-carbamate | m.p. 95–97° C. |
| 98 | Allyl-N-(3-(N-ethyl-N-(2-chloroethyl)-carbamoyloxy)-phenyl)-carbamate | m.p. 109–111° C. |
| 99 | sec.-Butyl-N-(3-(N,N-bis-(1-chloro-1-methylethyl)-carbamoyloxy)-phenyl)-carbamate | m.p. 74–76° C. |
| 100 | Allyl-N-(3-(N-ethyl-N-butylcarbamoyloxy)-phenyl)-carbamate | $n_D^{20} = 1.5361$ |
| 101 | Allyl-N-(3-(N-ethyl-N-phenylcarbamoyloxy)-phenyl)-carbamate | m.p. 93–94° C. |
| 102 | Allyl-N-(3-(N,N-bis-(1-chloro-1-methylethyl)-carbamoyloxy)-phenyl)-carbamate | m.p. 89–91° C. |
| 103 | Isopropyl-N-(3-(N-(2-chloropropyl-N-cyclohexyl-carbamoyloxy)-phenyl)-carbamate | m.p. 108–110° C. |
| 104 | Isopropyl-N-(3-(N-(4-methylphenyl)-N-propylcarbamoyloxy)-phenyl)-carbamate | $n_D^{20} = 1.5338$ |
| 105 | Isopropyl-N-(3-(N-(4-ethylphenyl)-N-propylcarbamoyloxy)-phenyl)-carbamate | $n_D^{20} = 1.5348$ |
| 106 | 2,2,2-Trichloroethyl-N-(3-(N-ethyl-N-(2-bromoethyl)-carbamoyloxy)-phenyl-carbamate | m.p. 98° C. |
| 107 | sec.-Butyl-N-(3-(N,N-di-sec.-butylcarbamoyloxy)-phenyl)-carbamate | m.p. 85–87° C. |
| 108 | Allyl-N-(3-(N,N-dibutylcarbamoyloxy)-phenyl)-carbamate | m.p. 62–65° C. |
| 109 | 1-Methylpropinyl-N-(3-(N-phenyl-N-isopropyl-carbamoyloxy)-phenyl)-carbamate | m.p. 131–135° C. |
| 110 | Allyl-N-(3-(N-phenyl-N-isopropyl-carbamoyloxy)-phenyl)-carbamate | m.p. 110–112° C. |
| 111 | 1-Methylpropinyl-N-(3-(N-phenyl-N-propyl-carbamoyloxy)-phenyl)-carbamate | m.p. 92–96° C. |
| 112 | Allyl-N-(3-(N-phenyl-N-propylcarbamoyloxy)-phenyl)-carbamate | m.p. 74–76° C. |
| 113 | Isopropyl-N-(3-(N-(2-bromoethyl)-N-butylcarbamoyloxy)-phenyl)-carbamate | $n_D^{20} = 1.5291$ |
| 114 | 1-Methylpropinyl-N-(3-N-ethyl-N-butylcarbamoyloxy)-phenyl)-carbamate | m.p. 85–87° C. |
| 115 | sec.-Butyl-N-(3-(N-ethyl-N-(3-chlorophenyl)-carbamoyloxy)-phenyl)-carbamate | m.p. 112–113° C. |
| 116 | Isopropyl-N-(3-(N-ethyl-N-(3-chlorophenyl)-carbamoyloxy)-phenyl)-carbamate | m.p. 125–126° C. |
| 117 | sec.-Butyl-N-(3-(N-methyl-N- | |

-continued

| Compound No. | Name of Compound | Physical Constants |
|---|---|---|
| | phenylcarbamoyloxy)-phenyl)-carbamate | $n_D^{20} = 1.5316$ |
| 118 | Isopropyl-N-(3-(N,N-dibutylcarbamoyloxy)-phenyl)-carbamate | m.p. 61–63° C. |
| 119 | Isopropyl-N-(3-(N-butyl-N-(2-chloroethyl)-carbamoyloxy)-phenyl)-carbamate | $n_D = 1.5085$ |
| 120 | Methyl-N-(3-(N-ethyl-N-(3-chlorophenyl)-carbamoyloxy)-phenyl)-carbamate | m.p. 104–106° C. |
| 121 | Methyl-N-(3-(N-methyl-N-(3,4-dichlorophenyl)-carbamoyloxy)-phenyl)-carbamate | m.p. 88–89° C. |
| 122 | Ethyl-N-(3-(N-ethyl-N-(3-chlorophenyl)-carbamoyloxy)-phenyl)-carbamate | m.p. 90–91° C. |
| 123 | Isopropyl-N-(3-N-cyclohexyl-N-(2-chloroethyl)-carbamoyloxy)-phenyl)-carbamate | $n_D^{40} = 1.5134$ |
| 124 | sec.-Butyl-N-(3-(N-methyl-N-(1-methylpropinyl)-carbamoyloxy)-phenyl)-carbamate | $n_D^{20} = 1.5046$ |
| 125 | Propyl-N-(3-(N,N-dimethylcarbamoyloxy)-phenyl)-carbamate | m.p. 98–99° C. |
| 126 | Propyl-N-(3-(N,N-dibutylcarbamoyloxy)-phenyl)-carbamate | $n_D^{20} = 1.5118$ |
| 127 | Propyl-N-(3-(N,N-dipropylcarbamoyloxy)-phenyl)-carbamate | $n_D^{20} = 1.5102$ |
| 128 | Isopropyl-N-(3-(N-methyl-N-(1-methyl-2-propinyl)-carbamoyloxy)-phenyl)-carbamate | m.p. 68–70° C. |
| 129 | Propyl-N-(3-ethyl-N-(3-methylphenyl)-carbamoyloxy)-phenyl)-carbamate | m.p. 116–117° C. |
| 130 | Propyl-N-(3-(N-ethyl-N-(4-methylphenyl)-carbamoyloxy)-phenyl)-carbamate | m.p. 70–71° C. |
| 131 | Propyl-N-(3-(N-ethyl-N-butyl-carbamoyloxy)-phenyl)-carbamate | $n_D^{20} = 1.5166$ |
| 132 | Isopropyl-N-(3-(N-isopropyl-N-(2-chloroethyl)-carbamoyloxy)-phenyl)-carbamate | m.p. 82–86° C. |
| 133 | Propyl-N-(3-(N-di-sec.-butyl-carbamoyloxy)-phenyl)-carbamate | $n_D^{20} = 1.4925$ |
| 134 | Isopropyl-N-(3-(N-tert.-butyl-N-2-chloroethylcarbamoyloxy)-phenyl)-carbamate | m.p. 69–71° C. |
| 135 | 3-Chloropropyl-N-(3-(N-phenyl-N-propyl-carbamoyloxy)-phenyl)-carbamate | m.p. 80° C. |
| 136 | sec.-Butyl-N-(3-N,N-diisobutyl-carbamoyloxy)-phenyl)-carbamate | m.p. 90–92° C. |
| 137 | sec.-Butyl-N-(3-(N,N-bis-(2-bromoethyl)-carbamoyloxy)-phenyl)-carbamate | m.p. 82–83° C. |
| 138 | 2-Bromoethyl-N-(3-N-phenyl-N-propyl-carbamoyloxy)-phenyl)-carbamate | m.p. 79–80° C. |
| 139 | 2-Chloroethyl-N-(3-(N-phenyl-N-propyl-carbamoyloxy)-phenyl)-carbamate | m.p. 84–85° C. |
| 140 | Isopropyl-N-(3-(N-phenyl-N-propylcarbamoyloxy)-phenyl)-carbamate | m.p. 82–83° C. |
| 141 | Propyl-N-(3-(N-phenyl-N-propyl-carbamoyloxy)-phenyl)-carbamate | m.p. 85–86° C. |
| 142 | 2-Chloro-1-methylethyl-N-(3-(N-(2-bromoethyl)-carbamoyloxy)-phenyl)-carbamate | m.p. 67–68° C. |
| 143 | sec.-Butyl-N-(3-(N-phenyl-N-propyl-carbamoyloxy)-phenyl)-carbamate | m.p. 65–67° C. |
| 144 | Isopropyl-N-(3-(N-benzyl-N-(2-hydroxyethyl)-carbamoyloxy)-phenyl)-carbamate | m.p. 70–72° C. |
| 145 | 2-Chloro-1-methylethyl-N-(3-(N-phenyl-N-propylcarbamoyloxy)-phenyl)-carbamate | m.p. 59–61° C. |
| 146 | sec.-Butyl-N-(3-(N,N-dibutyl-carbamoyloxy)-phenyl)-carbamate | m.p. 38–42° C. |
| 147 | sec.-Butyl-N-(3-(N-allyl-N-phenyl-carbamoyloxy)-phenyl)-carbamate | m.p. 43–46° C. |
| 148 | 3-Chloropropyl-N-(3-(N-phenyl-N- | |

-continued

| Compound No. | Name of Compound | Physical Constants |
|---|---|---|
| | allylcarbamoyloxy)-phenyl)-carbamate | m.p. 64° C. |
| 149 | Isopropyl-N-(3-(N-isopropyl-N-(2-bromoethyl)-carbamoyloxy)-phenyl)-carbamate | m.p. 78–80° C. |
| 150 | Isopropyl-N-(3-(N-benzyl-N-(2-chloroethyl)-carbamoyloxy)-phenyl)-carbamate | m.p. 106–108° C. |
| 151 | Propyl-N-)3-(N,N-bis-(2-bromoethyl)-carbamoyloxy)-phenyl)-carbamate | m.p. 55–56° C. |
| 152 | 2-Chloro-1-methylethyl-N-(3-(N,N-dimethyl-carbamoyloxy)-phenyl)-carbamate | m.p. 85–87° C. |
| 153 | Propyl-N-(3-(N,N-diisobutyl-carbamoyloxy)-phenyl)-carbamate | m.p. 79–80° C. |
| 154 | Propyl-N-(3-(N,N-diethylcarbamoyloxy)-phenyl)-carbamate | m.p. 57–58° C. |
| 155 | 2-Chloro-1-methylethyl-N-(3-(N-methyl-N-phenylcarbamoyloxy)-phenyl)-carbamate | m.p. 82–84° C. |
| 156 | 2-Chloro-1-methylethyl-N-(3-(N,N-diethyl-carbamoyloxy)-phenyl)-carbamate | m.p. 76–77° C. |
| 157 | sec.-Butyl-N-(3-(N-tert.-butyl-N-(2-chloroethyl)-carbamoyloxy)-phenyl)-carbamate | m.p. 74–75° C. |
| 158 | sec.-Butyl-N-(3-(N-2-bromoethyl)-N-isopropylcarbamoyloxy)-phenyl)-carbamate | m.p. 86–87° C. |
| 159 | Isopropyl-N-(3-(N-(3-methylphenyl)-N-propylcarbamoyloxy)-phenyl-carbamate | m.p. 101° C. |
| 160 | Isopropyl-N-(3-(N-(3-methoxyphenyl)-N-propylcarbamoyloxy)-phenyl)-carbamate | m.p. 102° C. |
| 161 | Isopropyl-N-(3-(N,N-diethylcarbamoyloxy)-phenyl)-carbamate | m.p. 95–96° C. |
| 162 | Isopropyl-N-(3-(N-(2-methylphenyl)-N-propyl-carbamoyloxy)-phenyl)-carbamate | m.p. 98–99° C. |
| 163 | Isopropyl-N-(3-(N-(3-methylphenyl)-N-butyl-carbamoyloxy)-phenyl)-carbamate | m.p. 91–92° C. |
| 164 | Isopropyl-N-(3-(N-isobutyl-N-methylcarbamoxyloxy)-phenyl)-carbamate | m.p. 88–89° C. |
| 165 | sec.-Butyl-N-(3-(N-(4-ethylphenyl)-N-methylcarbamoyloxy)-phenyl)-carbamate | $n_D^{20} = 1.5520$ |
| 166 | sec.-Butyl-N-(3-(N-isopropyl-N-(2-chloroethyl)-carbamoyloxy)-phenyl)-carbamate | m.p. 93–94° C. |
| 167 | sec.-Butyl-N-(3-(N-(2-phenylethyl)-N-methyl-carbamoyloxy)-phenyl)-carbamate | $n_D^{20} = 1.5400$ |
| 168 | sec.-Butyl-N-(3-(N-ethyl-N-(4-methylphenyl)-carbamoyloxy)-phenyl)-carbamate | $n_D^{20} = 1.5410$ |
| 169 | Allyl-N-(3-(N-allyl-N-phenyl-carbamoyloxy)-phenyl)-carbamate | m.p. 60° C. |

These compounds are soluble in acetone, cyclohexanone, acetic ester, isophorone, ether and tetrahydrofurane, and are practically insoluble in water and light benzine. The starting products required for the production of the compounds to be used according to the invention can be produced by methods known in the art. These starting products are listed in the following table.

| | |
|---|---|
| (3-Hydroxycarbanilic acid)-3-chloropropyl ester | m.p. 72–74° C. |
| (3-Hydroxycarbanilic acid)-2-chloro-1-methyl ester | m.p. 76–28° C. |
| (3-Hydroxycarbanilic acid)-2-bromethyl ester | m.p. 62–63° C. |
| Chloroformic acid ester of (3-hydroxycarbanilic acid)-3-chloropropyl ester | $n_D^{20} = 1.5390$ |
| Chloroformic acid ester of (3-hydroxycarbanilic acid)-2-chloro-1-methyl ester | $n_D^{20} = 1.5329$ |
| Chloroformic acid ester of (3-hydroxycarbanilic acid)-2-bromethyl ester | $n_D^{20} = 1.5612$ |
| Chloroformic acid ester of 3-hydroxycarbanilic acid-isopropyl ester | $n_D^{20} = 1.5215$ |
| Chloroformic acid ester of 3-hydroxycarbanilic acid-ethyl ester | m.p. 40–42° C. |
| Chloroformic acid ester of 3-hydroxycarbanilic acid-sec.-butyl ester | $n_D^{40} = 1.5106$ |
| Chloroformic acid ester of 3-hydroxycarbanilic acid-2-chlorethyl ester | $n_D^{20} = 1.5422$ |
| Chloroformic acid ester of 3-hydroxycarbanilic | |

-continued

| | |
|---|---|
| acid-n-propyl ester | m.p. 51-54° C. |

The following examples will illustrate but not restrict the invention.

EXAMPLE 1

In the greenhouse, the plants listed below were treated in the post-emergence stage with an applied volume of 3 kg of active substance per hectare. The comparison agents were:

1. N-(3-trifluoromethylphenyl)-N',N'-dimethyl urea,
2. 3-Methoxycarbonylaminophenyl-N-(3-methylphenyl)carbamate.

The plants were in the young stage. The agents were applied as emulsions; comparison agent No. 1 was applied as a suspension. The applied amount of liquid corresponded to 500 liter/ha. The result of the treatment was rated after 14 days (0=total destruction, 10=no damage).

The values in the following table illustrate the good tolerance of the agents of the invention, while the known comparison agents considerably damaged the cultivated plants.

| Agent of Invention | kg/ha active substance | Cotton | Soybean | Corn | Wheat | Barley | Rye | Oats | Stellaria media | Senecio vulgaris | Matricaria chamomilla | Lamium amplexicaule | Centaurea cyanus | Amaranthus retroflexus | Chrysanthemum segetum |
|---|---|---|---|---|---|---|---|---|---|---|---|---|---|---|---|
| n-Propyl-N-(3-N,N-di-sec.-butyl-carbamoyloxy)-phenyl)-carbamate | 3 | 10 | — | 10 | 10 | 10 | 10 | 10 | 0 | — | — | 0 | 5 | 1 | — |
| 2,2,2-Trichloroethyl-N-(3-(N-icopropyl-N-phenylcarbamoyloxy)-phenyl)-carbamate | 3 | 9 | 0 | 8 | 10 | 10 | 10 | 10 | 0 | — | — | 1 | 2 | 0 | — |
| Isopropyl-N-(3-(N-ethyl-N-(2-chloroethyl)-carbamoyloxy)-phenyl)-carbamate | 1 | 8 | — | 10 | 10 | 10 | 10 | 10 | 0 | 0 | 3 | 0 | 0 | 0 | 0 |
| Isopropyl-N-(3-(N-methyl-N-(2-chloroethyl)-carbamoyloxy)-phenyl)-carbamate | 1 | 10 | 9 | 10 | 10 | 10 | 10 | 10 | 0 | 5 | — | 0 | 1 | 1 | 4 |
| Ethyl-N-(3-(N-allyl-N-phenylcarbamoyloxy)-phenyl)-carbamate phenyl)-carbamate | 1 | 10 | 8 | 10 | 10 | 10 | 10 | 10 | 0 | — | — | 0 | — | 0 | — |
| Ethyl-N-(3-(N-allyl-N-(2-methylphenyl)-carbamoyloxy)-phenyl)-carbamate | 6 | 10 | 8 | 10 | 10 | 10 | 10 | 10 | 0 | — | — | 0 | — | 0 | — |
| Isopropyl-N-(3-(N,N-diallylcarbamoyloxy)-phenyl)-carbamate phenyl)-carbamate | 1 | 10 | 8 | 10 | 10 | 10 | 10 | 10 | 0 | — | — | 0 | — | 4 | 5 |

| Agent of Invention | Ipomoea purpurea | Polygonum pathifolium | Brassica oleracea | Beta vulgaris | Solanum lycopersicum | Allium sativum | Cucumis sativus | Medicago sativa | Helianthus annus | Lactuca capitata | Trifolium spp. | Spinaia oleracea | Setaria italica |
|---|---|---|---|---|---|---|---|---|---|---|---|---|---|
| n-Propyl-N-(3-(N,N-di-sec.-butyl-carbamoyloxy)-phenyl)-carbamate | 4 | 6 | 0 | 1 | 0 | — | 0 | — | 3 | 0 | 4 | — | — |
| 2,2,2-Trichloroethyl-N-(3-N-isopropyl)-N-phenylcarbamoyloxy)-phenyl)-carbamate | 1 | 0 | 0 | 0 | 0 | — | 0 | 2 | 1 | 0 | 1 | — | — |
| Isopropyl-N-(3-N-ethyl-N-(2-chloroethyl)-carbamoyloxy)-phenyl)-carbamate | 0 | 0 | 0 | 0 | 0 | 0 | 0 | 0 | 0 | — | — | 0 | 0 |
| Isopropyl-N-(3-(N-methyl-N-(2-chloroethyl)-carbamoyloxy)-phenyl)-carbamate | 0 | 0 | 0 | 1 | 0 | 0 | 0 | 0 | 0 | 1 | 1 | 0 | 3 |
| Ethyl-N-(3-(N-allyl-N-phenylcarbamoyloxy)-carbamate | 0 | 1 | 0 | 0 | 1 | 0 | 0 | 2 | 1 | 0 | 0 | 4 | 2 |
| Ethyl-N-(3-(N-allyl-N-(2-methylphenyl)-carbamoyloxy)-phenyl)-carbamate | 0 | 0 | 0 | 0 | 0 | 2 | 0 | 2 | 0 | 0 | 0 | — | — |
| Isopropyl-N-(3-(N,N-diallylcarbamoyloxy)-phenyl)-carbamate | 0 | 1 | 0 | 0 | 4 | — | — | — | 2 | 0 | 0 | — | — |

-continued

| Agent of Invention | stance | ton | bean | Corn | Wheat | ley | Rye | Oats | dia | garis | illa | caule | cyanus | us | getum |
|---|---|---|---|---|---|---|---|---|---|---|---|---|---|---|---|
| Isopropyl-N-(3-(N-ethyl-N-isopropyl carbamoyloxy)-phenyl)-carbamate | 3 | 10 | — | 10 | 10 | 10 | 10 | 10 | 3 | — | — | 3 | — | — | — |
| Isopropyl-N-(3-(N-butyl-N-ethylcarbamoyloxy)-phenyl)-carbamate | 1 | 10 | — | 10 | 10 | 10 | 10 | 10 | 2 | 4 | 3 | 0 | 1 | 0 | 1 |
| Isopropyl-N-(3-(N,N-diisopropylcarbamoyloxy)-phenyl-carbamate | 1 | 10 | — | 10 | 10 | 9 | 10 | 10 | 0 | 1 | — | 0 | 0 | 0 | — |
| Isopropyl-N-(3-(N-butyl-N-phenyl-carbamoyloxy)-phenyl)-carbamate | 1 | 10 | — | 10 | 10 | 10 | 10 | 10 | 0 | 2 | — | 0 | 3 | 0 | 2 |
| Ethyl-N-(3-(N-ethyl-N-phenyl-carbamoyloxy)-phenyl)-carbamate | 1 | 8 | — | 10 | 10 | 10 | 10 | 10 | 1 | 4 | 3 | 0 | 2 | 0 | — |
| Isopropyl-N-(3-(N-ethyl-N-phenyl-carbamoyloxy)-phenyl)-carbamate | 1 | 10 | — | 10 | 10 | 10 | 10 | 10 | 0 | 2 | 0 | 0 | 0 | 0 | 0 |
| Isopropyl-N-(3-(N-cyclohexyl-N-methylcarbamoyloxy)-phenyl)-carbamate | 1 | 10 | — | 10 | 10 | 10 | 10 | 10 | 0 | 5 | 4 | 0 | 1 | 0 | 0 |
| Isopropyl-N-(3-(N-allyl-N-phenyl-carbamoyloxy)-phenyl)-carbamate | 1 | 10 | — | 10 | 10 | 10 | 10 | 10 | 3 | 3 | 3 | 0 | 4 | 4 | — |

| Agent of Invention | Ipomoea purpurea | Polygonum pathifolium | Brassica oleracea | Beta vulgaris | Solanum lycopersicum | Allium sativum | Cucumis sativus | Medicago sativa | Helianthus annus | Lactuca capitata | Trifolium spp. | Spinaia oleracea | Setaria italica |
|---|---|---|---|---|---|---|---|---|---|---|---|---|---|
| Isopropyl-N-(3-(N-ethyl-N-isopropylcarbamoyloxy)-phenyl)-carbamate | 1 | 5 | 1 | 2 | 6 | — | 1 | 0 | 4 | 3 | 1 | — | 3 |
| Isopropyl-N-(3-(N-butyl-N-ethylcarbamoyloxy)-phenyl)-carbamate | 0 | 0 | 0 | 0 | 1 | 0 | 0 | 3 | 0 | 0 | 0 | 1 | 1 |
| Isopropyl-N-(3-(N,N-diisopropylcarbamoyloxy)-phenyl)-carbamate | 0 | 0 | 0 | 0 | 0 | 0 | 0 | 0 | 0 | 0 | 0 | 0 | 1 |
| Isopropyl-N-(3-(N-butyl-N-phenyl-carbamoyloxy)-phenyl)-carbamate | 0 | 0 | 0 | 1 | 0 | 0 | 0 | 0 | 0 | 0 | 0 | 0 | 0 |
| Ethyl-N-(3-(N-ethyl-N-phenylcarbamoyloxy)-phenyl)-carbamate | 0 | 0 | 0 | 0 | 0 | 4 | 0 | 0 | 0 | 0 | 0 | 4 | — |
| Isopropyl-N-(3-(N-ethyl-N-phenylcarbamoyloxy)-phenyl)-carbamate | 0 | 0 | 0 | 0 | 0 | 1 | 0 | 0 | 0 | 0 | 0 | 0 | 2 |
| Isopropyl-N-(3-N-(cyclohexyl-N-methylcarbamoyloxy)-phenyl)-carbamate | 0 | 0 | 0 | 0 | 0 | 0 | 1 | 0 | 0 | 0 | 0 | 0 | 0 |
| Isopropyl-N-(3-(N-allyl-N-phenyl-carbamoyloxy)-phenyl)-carbamate | — | 2 | — | 1 | 0 | — | 0 | 1 | 4 | 1 | 1 | 0 | 5 |

| Agent of Invention | kg/ha active substance | Cotton | Soybean | Corn | Wheat | Barley | Rye | Oats | Stellaria media | Senecio vulgaris | Matricaria chamomilla | Lamium amplexicaule | Centaurea cyanus | Amaranthus retroflexus | Chrysanthemum segetum |
|---|---|---|---|---|---|---|---|---|---|---|---|---|---|---|---|
| Isopropyl-N-(3-(N-methyl-N-phenyl-carbamoyloxy)-phenyl)-carbamate | 1 | 10 | 1 | 10 | 10 | 10 | 10 | 10 | 0 | 0 | 0 | 0 | 0 | 0 | 0 |
| Isopropyl-N-(3-N-(cyclohexyl-N-isobutylcarbamoyloxy)-phenyl)-carbamate | 1 | 10 | 8 | 10 | 10 | 10 | 10 | 10 | 0 | 1 | 1 | 0 | 0 | 1 | 0 |
| Isopropyl-N-(3-(N-cyclohexyl-N-propylcarbamoyloxy)-phenyl)-carbamate | 1 | 10 | 8 | 10 | 10 | 10 | 10 | 10 | 3 | — | — | 1 | 2 | — | 2 |
| Isopropyl-N-(3-(N-cyclohexyl-N-isopropylcarbamoyloxy)-phenyl)-carbamate | 1 | 10 | 10 | 10 | 10 | 10 | 10 | 10 | 4 | — | — | 0 | — | — | — |
| Isopropyl-N-(3-(N-butyl-N-cyclohexylcarbamoyloxy)-phenyl)-carbamate | 1 | 10 | 10 | 10 | 10 | 10 | 10 | 10 | 1 | — | — | 0 | — | 5 | — |
| Isopropyl-N-(3-(methyl-N-phenethylcarbamoyloxy)-phenyl)-carbamate | 1 | 10 | 8 | 10 | 10 | 10 | 10 | 10 | 1 | — | — | 2 | — | 1 | — |
| Isopropyl-N-(3-(N-benzyl-N-methylcarbamoyl- | 1 | 10 | — | 10 | 10 | 10 | 10 | 9 | 0 | — | — | 0 | 2 | 0 | 2 |

-continued

| Agent of Invention | Ipomoea purpurea | Polygonum pathifolium | Brassica oleracea | Beta vulgaris | Solanum lycopersicum | Allium sativum | Cucumis sativus | Medicago sativa | Helianthus annus | Lactuca capitata | Trifolium spp. | Spinaia oleracea | Setaria italica |
|---|---|---|---|---|---|---|---|---|---|---|---|---|---|
| Isopropyl-M-(3-N-methyl-N-phenyl-carbamoyloxy)-phenyl)-carbamate | 0 | 0 | 0 | 0 | 0 | 3 | 0 | 0 | 0 | 2 | 4 | 3 | 3 |
| Isopropyl-N-(3-N-cyclohexyl-N-isobutylcarbamoyloxy)-phenyl)-carbamate | 0 | 0 | 0 | 0 | 5 | 0 | 0 | 0 | 0 | 2 | 0 | 0 | 4 |
| Isopropyl-N-(3-(N-cyclohexyl-N-propyl-(carbamoyloxy)-phenyl)-carbamate | 4 | — | — | 3 | — | 1 | 0 | 2 | 0 | 0 | 0 | — | — |
| Isopropyl-N-3-(N-cyclohexyl-N-iso-propylcarbamoyloxy)-phenyl)-carbamate | 1 | 3 | 0 | 2 | — | — | 0 | 2 | — | — | 0 | — | — |
| Isopropyl-N-3-(N-butyl-N-cyclohexyl-carbamoyloxy)-phenyl)-carbamate | 4 | 2 | 1 | — | — | — | 1 | 0 | 0 | 2 | 0 | 1 | — |
| Isopropyl-N-3-(N-methyl-N-phenethyl-carbamoyloxy)-phenyl)-carbamate | 2 | 1 | 1 | 4 | 2 | — | 0 | — | 3 | 5 | 4 | 4 | 3 |
| Isopropyl-N-3-(N-benzyl-N-methyl-carbamoyloxy)-phenyl)-carbamate | 0 | 0 | 0 | 0 | 0 | 2 | 0 | 0 | 0 | 0 | 0 | 0 | 0 |

| Agent of Invention | kg/ha active substance | Cotton | Soybean | Corn | Wheat | Barley | Rye | Oats | Stellaria media | Senecio vulgaris | Matricaria chamomilla | Lamium amplexicaule | Centaurea cyanus | Amaranthus retroflexus | Chrysanthemum segetum |
|---|---|---|---|---|---|---|---|---|---|---|---|---|---|---|---|
| Isopropyl-N-(3-(N-ethyl-N-benzyl)-carbamoyloxy)-phenyl)-carbamate | 1 | 10 | — | 10 | 10 | 10 | 10 | — | 4 | — | 5 | 5 | 2 | 0 | 1 |
| Isopropyl-N-(3-(N,N-bis-(2-chloroethyl)-carbamoyloxy)-phenyl)-carbamate | 1 | — | — | 9 | 9 | — | — | 0 | 0 | 0 | 0 | 0 | 0 | 0 | 0 |
| Isopropyl-N-(3-(N-sec.-butyl-N-cyclohexyl-carbamoyloxy)-phenyl)-carbamate | 1 | — | — | — | 10 | 10 | 9 | 10 | 0 | 1 | 0 | 0 | 0 | 0 | 0 |
| sec.-Butyl-N-(3-N-ethyl-N-pentylcarbamoyloxy)-phenyl)-carbamate | 1 | — | — | 10 | 10 | 10 | 10 | — | 0 | 0 | — | 0 | 0 | 0 | 0 |
| 3-Chloropropyl-N-(3-(N-ethyl-N-phenylcarbamoyloxy)-phenyl)-carbamate | 1 | 10 | 8 | 10 | 10 | 10 | 10 | 9 | 3 | 6 | — | — | 0 | 0 | 0 |
| 2-Chlor-1-methylethyl-N-(3-(N-ethyl-N-phenyl-carbamoyloxy)-phenyl)-carbamate | 1 | 10 | — | 10 | 10 | 10 | 10 | 10 | 0 | 4 | 2 | 0 | 1 | 0 | 0 |
| 2-Chlor-1-methylethyl-N-(3-(N-butyl-N-phenyl-carbamoyloxy)-phenyl)-carbamate | 1 | 10 | — | 10 | 10 | 10 | 10 | 10 | 1 | — | — | 0 | — | 0 | 2 |

| Agent of Invention | Ipomoea purpurea | Polygonum pathifolium | Brassica oleracea | Beta vulgaris | Solanum lycopersicum | Allium sativum | Cucumis sativus | Medicago sativa | Helianthus annus | Lactuca capitata | Trifolium spp. | Spinaia oleracea | Setaria italica |
|---|---|---|---|---|---|---|---|---|---|---|---|---|---|
| Isopropyl-N-(3-(N-ethyl-N-benzylcarbamoyloxy)-phenyl)-carbamate | — | 3 | — | — | — | — | 3 | 3 | — | — | 1 | — | 2 |
| Isopropyl-N-(3-(N,N bis-(2-chloroethyl)-carbamoyloxy)-phenyl)-carbamate | 0 | 0 | 0 | 0 | 0 | 0 | 0 | 0 | 0 | 0 | 0 | 0 | 1 |
| Isopropyl-N-(3-(N-sec.-butyl-N-cyclohexyl-carbamoyloxy)-phenyl)-carbamate | 0 | 0 | 1 | 0 | 0 | 0 | 0 | 0 | 0 | 0 | 0 | 0 | 0 |
| sec.-Butyl-N-(3-(N-ethyl-N-phenyl-carbamoyloxy)-phenyl)-carbamate | 1 | 0 | 0 | 1 | 1 | 0 | 0 | 0 | 0 | 0 | 0 | 0 | 1 |
| 3-Chlorpropyl-N-(3-(N-ethyl-N-phenyl-carbamoyloxy)-phenyl)-carbamate | 6 | 0 | — | — | 2 | 2 | 0 | 4 | 0 | 0 | 1 | 1 | 3 |
| 2-Chloro-1-methylethyl-N-(3-N-ethyl-N-phenylcarbamoyloxy)-phenyl)-carbamate | 0 | 1 | 0 | 0 | 1 | — | 0 | 0 | 0 | 3 | 0 | 0 | 0 |
| 2-Chloro-1-methylethyl-N-(3-(N-butyl-N-phenylcarbamoyloxy)-phenyl)-carbamate | 4 | 3 | 0 | 2 | 3 | — | 0 | 3 | 0 | 1 | 3 | — | 2 |

-continued

| Agent of Invention | kg/ha active substance | Cotton | Soybean | Corn | Wheat | Barley | Rye | Oats | Stellaria media | Senecio vulgaris | Matricaria chamomilla | Lamium amplexicaule | Centaurea cyanus | Amaranthus retroflexus | Chrysanthemum segetum |
|---|---|---|---|---|---|---|---|---|---|---|---|---|---|---|---|
| 3-Chloropropyl-N-(3-(N,N-bis-(2-chloroethyl)-carbamoyloxy)-phenyl)-carbamate | 1 | — | — | 9 | 10 | 10 | 9 | 9 | 0 | 0 | 2 | 0 | 0 | 0 | 0 |
| 2-Chloroethyl-N-(3-(N,N-bis-(2-chloroethyl)-carbamoyloxy)-phenyl)-carbamate | 1 | 10 | 8 | 10 | 10 | 10 | 10 | 10 | 0 | — | 3 | 0 | 1 | 0 | 1 |
| sec-Butyl-N-(3-(N,N-bis-(2-chloroethyl)-carbamoyloxy)-phenyl)-carbamate | 1 | 8 | — | 10 | 10 | 10 | 10 | 9 | 1 | 2 | 0 | 0 | 3 | 0 | 0 |
| 2-Chloroethyl-N-(3-(N-ethyl-N-phenylcarbamoyloxy)-phenyl)-carbamate | 1 | 8 | 8 | 10 | 10 | 10 | 10 | 10 | 0 | 0 | 0 | 0 | 0 | 0 | 0 |
| 2-Chlor-1-methylethyl-N-(3-(N,N-bis-(2-chloroethyl)-carbamoyloxy)-phenyl)-carbamate | 1 | — | — | 10 | 10 | 10 | 10 | 10 | 0 | 1 | 1 | 0 | 0 | 0 | 0 |
| n-Propyl-N-(3-(N-butyl-N-phenylcarbamoyloxy)-phenyl)-carbamate | 1 | 10 | — | 10 | 10 | — | 10 | — | 0 | 0 | 1 | 0 | 0 | 0 | 0 |
| n-Propyl-N-(3-(3-(N,N-bis-(2-chloroethyl)-carbamoyloxy)-phenyl)-bamate | 1 | 8 | 8 | 10 | 10 | 10 | — | — | 0 | 0 | 0 | 0 | 0 | 0 | 0 |

| Agent of Invention | Ipomoea purpurea | Polygonum lapathifolium | Brassica oleracea | Beta vulgaris | Solanum lycopersicum | Allium sativum | Cucumis sativus | Medicago sativa | Helianthus annus | Lactuca capitata | Trifolium spp. | Spinaia oleracea | Setaria italica |
|---|---|---|---|---|---|---|---|---|---|---|---|---|---|
| 3-Chloropropyl-N-(3-(N,N-bis-(2-chloroethyl)-carbamoyloxy)-phenyl)-carbamate | 0 | 0 | 0 | 0 | 0 | 0 | 0 | 0 | 0 | 0 | 0 | 0 | 0 |
| 2-Chloroethyl-N-(3-(N,N-bis-(2-chloroethyl)-carbamoyloxy)-phenyl)-carbamate | 3 | 0 | 0 | 0 | 1 | 5 | 1 | 0 | 0 | 0 | 1 | 0 | — |
| sec.-Butyl-N-(3-(N,N-bis-(2-chloroethyl)-carbamoyloxy)-phenyl)-carbamate | 1 | 0 | 2 | 0 | 2 | 3 | 0 | 0 | 0 | 0 | 1 | 0 | 2 |
| 2-Chloroethyl-N-(3-(N-ethyl-N-phenyl-carbamoyloxy)-phenyl)-carbamate | 0 | 0 | 0 | 0 | 0 | 0 | 0 | 0 | 0 | 0 | 0 | 0 | 0 |
| 2-Chloro-1-methylethyl-N-(3-(N,N-bis-(2-chloroethyl)-carbamoyloxy)-phenyl)-carbamate | 0 | 0 | 0 | 0 | 0 | 1 | 0 | 0 | 0 | 0 | 0 | 0 | 0 |
| n-Propyl-N-(3-(N-butyl-N-phenyl-carbamoyloxy)-phenyl)-carbamate | 0 | 0 | 0 | 0 | 4 | 0 | 0 | 0 | 0 | 0 | 0 | 0 | 0 |
| n-Propyl-N-(3-(N,N-bis-(2-chloroethyl)-carbamoyloxy)-phenyl)-carbamate | 0 | 0 | 0 | 0 | 0 | 0 | 0 | 0 | 0 | 1 | 0 | 0 | 0 |

| Agent of Invention | kg/ha active substance | Cotton | Soybean | Corn | Wheat | Barley | Rye | Oats | Stellaria media | Senecio vulgaris | Matricaria chamomilla | Lamium amplexicaule | Centaurea cyanus | Amaranthus retroflexus | Chrysanthemum segetum |
|---|---|---|---|---|---|---|---|---|---|---|---|---|---|---|---|
| Ethyl-N-(3-(N-ethyl-N-(4-methylphenyl)-carbamoyloxy)-phenyl)-carbamate | 1 | 10 | — | 10 | 10 | — | 10 | — | 0 | 2 | — | 0 | 1 | 0 | 1 |
| Ethyl-N-(3-(N-ethyl-N-(3-methylphenyl)-carbamoyloxy)-phenyl)-carbamate | 1 | 10 | — | 10 | 10 | 10 | 10 | 10 | 0 | — | 3 | 2 | 0 | 0 | 0 |
| Ethyl-N-(3-(N-ethyl-N-(2-methylphenyl)-carbamoyloxy)-phenyl)-carbamate | 1 | 10 | — | 10 | 10 | 10 | 10 | 10 | 1 | — | 2 | 0 | 4 | 1 | 0 |
| Isopropyl-N-(3-(N-methyl-N-(4-methylphenyl)-carbamoyloxy)-phenyl-carbamate | 1 | 8 | — | 10 | 10 | 10 | 10 | 10 | 0 | 0 | 3 | 0 | 0 | 0 | 0 |
| Isopropyl-N-(3-(N-methyl-N-(2-methylphenyl)- | | | | | | | | | | | | | | | |

-continued

| Agent of Invention | | | | | | | | | | | | | | | |
|---|---|---|---|---|---|---|---|---|---|---|---|---|---|---|---|
| carbamoyloxy-phenyl)-carbamate | | | | | | | | | | | | | | | |
| Isopropyl-N-(3(-N-ethyl-N-(4-methylphenyl)-carbamoyloxy)-phenyl)-carbamate | 3 | — | — | 8 | 10 | 10 | 10 | 10 | 0 | 0 | 0 | 0 | 0 | 0 | 0 |
| n-Propyl-N-(3-(N-ethyl-N-phenylcarbamoyloxy)-phenyl)-carbamate | 1 | 10 | 8 | 10 | 10 | 10 | 10 | 10 | 0 | 2 | 0 | 0 | 1 | 1 | 0 |
| sec.-Butyl-N-(3-(N-butyl-N-phenylcarbamoyloxy)-phenyl)-carbamate | 3 | 10 | 10 | 10 | 10 | 10 | 10 | 10 | 2 | — | — | 0 | 2 | 1 | 2 |

| Agent of Invention | Ipomoea purpurea | Polygonum lapathifolium | Brassica oleracea | Beta vulgaris | Solanum lycopersicum | Allium sativum | Cucumis sativus | Medicago sativa | Helianthus annus | Lactuca capitata | Trifolium spp. | Spinaia oleracea | Setaria italica |
|---|---|---|---|---|---|---|---|---|---|---|---|---|---|
| Ethyl-N-(3-(N-ethyl-N-(4-methylphenyl)-carbamoyloxy)-phenyl)-carbamate | 1 | 0 | 0 | 0 | 0 | 0 | 0 | 0 | 0 | 0 | 1 | 0 | 4 |
| Ethyl-N-(3-(N-ethyl-N-(3-methylphenyl)-carbamoyloxy)-phenyl)-carbamate | 3 | 0 | 2 | 1 | 4 | 2 | — | 0 | 0 | 0 | 0 | 1 | 1 |
| Ethyl-N-(3-(N-ethyl-N-(2-methylphenyl)-carbamoyloxy)-phenyl)-carbamate | — | 0 | 0 | 1 | 0 | 3 | — | 0 | 0 | 1 | 0 | 0 | — |
| Isopropyl-N-(3-(N-methyl-N-(4-methylphenyl)-carbamoyloxy)-phenyl)-carbamate | 0 | 0 | 1 | 0 | 4 | 4 | 1 | 0 | 0 | 0 | 0 | 0 | 0 |
| Isopropyl-N-(3-(N-methyl-N-(2-methylphenyl)-carbamoyloxy)-phenyl)-carbamate | 0 | 0 | 0 | 0 | 0 | 0 | 0 | 0 | 0 | 0 | 0 | 0 | 0 |
| Isopropyl-N-(3-(N-ethyl-N-(4-methylphenyl)-carbamoyloxy)-phenyl)-carbamate | 0 | 0 | 0 | 0 | 0 | 0 | 0 | 0 | 0 | 0 | 0 | 0 | 1 |
| n-Propyl-N-(3-(N-ethyl-N-phenylcarbamoyloxy)-phenyl)-carbamate | 6 | 1 | 0 | 1 | 1 | 0 | 0 | 0 | 3 | 0 | 0 | 0 | — |
| sec.-Butyl-N-(3-(N-butyl-N-phenylcarbamoyloxy)-phenyl)-carbamate | — | — | 0 | 0 | 8 | — | 0 | 0 | 2 | 0 | 0 | 1 |

| Agent of Invention | kg/ha active substance | Cotton | Soybean | Corn | Wheat | Barley | Rye | Oats | Stellaria media | Senecio vulgaris | Matricaria chamomilla | Lamium amplexicaule | Centaurea cyanus | Amaranthus retroflexus | Chrysanthemum segetum |
|---|---|---|---|---|---|---|---|---|---|---|---|---|---|---|---|
| Propyl-N-(3-(N-ethyl-N-isopropyl)-carbamoyloxy)-phenyl)-carbamate | 3 | — | — | 9 | 7 | 7 | — | — | 0 | — | — | 0 | 5 | 0 | 7 |
| Isopropyl-N-(3-(N,N-diisobutylcarbamoyloxy)-phenyl)-carbamate | 3 | 10 | — | 10 | 10 | 10 | — | — | 5 | — | 0 | 2 | 8 | — | 5 |
| sec.-Butyl-N-(3-(N-isobutyl-N-methylcarbamoyloxy)-phenyl)-carbamate | 3 | — | — | 8 | 10 | 10 | — | — | 0 | 5 | 0 | 0 | 0 | 0 | 0 |
| 2-Chloroethyl-N-(3-(N-ethyl-N-butylcarbamoyloyx)-phenyl)-carbamate | 3 | 10 | 9 | 10 | 10 | 10 | — | — | 3 | — | — | 0 | 8 | 3 | 5 |
| 2-Chloroethyl-N-(3-(N-methyl-N-phenyl)-carbamoyloxy)-phenyl)-carbamate | 3 | 8 | — | 10 | 10 | 10 | — | — | 0 | — | — | 0 | 3 | 0 | 0 |
| 2-Chloroethyl-N-(3-(N-allyl-N-phenylcarbamoyloxy)-phenyl)-carbamate | 3 | 8 | — | 10 | 10 | 10 | — | — | 0 | 3 | 5 | 0 | 2 | 0 | 0 |

| Agent of Invention | Ipomoea purpurea | Polygonum lapathifolium | Brassica oleracea | Beta vulgaris | Solanum lycopersicum | Allium sativum | Cucumis sativus | Medicago sativa | Helianthus annus | Lactuca capitata | Trifolium spp. | Spinaia oleracea | Setaria italica |
|---|---|---|---|---|---|---|---|---|---|---|---|---|---|
| Propyl-N-(3-(N-ethyl-N-isopropylcarbamoyloxy)-phenyl)-carbamate | 0 | 0 | 0 | 0 | 0 | 1 | 0 | 0 | 1 | — | — | — | 1 |
| Isopropyl-N-(3-(N,N-diisobutylcarbamoyloxy)-phenyl)-carbamate | 5 | 5 | — | 2 | — | 5 | 4 | 3 | 8 | — | — | — | — |
| sec.-Butyl-N-(3-(N-isobutyl-N-methylcarbamoyloxy)-phenyl)-carbamate | 0 | 0 | 0 | 0 | 0 | 1 | 0 | 0 | 0 | — | — | — | 5 |
| 2-Chloroethyl-N-(3-(N-ethyl-N-butylcarbamoyloxy)-phenyl)-carbamate | 7 | 3 | 1 | 5 | 5 | — | 0 | 7 | — | — | — | — | 3 |
| 2-Chloroethyl-N-(3-(N-methyl-N-phenyl-carbamoyloxy)-phenyl)-carbamate | 0 | 0 | 0 | 0 | 3 | 7 | 0 | 0 | 0 | — | — | — | 0 |
| 2-Chloroethyl-N-(3-(N-allyl-N-phenylcarbamoyloxy)-phenyl)-carbamate | 0 | 0 | 0 | 0 | 4 | 3 | 0 | 0 | 0 | — | — | — | 0 |

-continued

| Agent of Invention | kg/ha active substance | Cotton | Soybean | Corn | Wheat | Barley | Rye | Oats | Stellaria media | Senecio vulgaris | Matricaria chamomilla | Lamium amplexicaule | Centaurea cyanus | Amaranthus retroflexus | Chrysanthemum segetum |
|---|---|---|---|---|---|---|---|---|---|---|---|---|---|---|---|
| sec.-Butinyl-n-(3-(N-methyl-N-phenylcarbamoyloxy)-phenyl)-carbamate | 3 | — | — | 10 | 9 | 9 | — | — | 0 | 4 | 5 | 0 | 0 | 0 | 0 |
| sec.-Butinyl-N-(3-(N-ethyl-N-ethyl-N-phenyl-carbamoyloxy)-phenyl)-carbamate | 3 | 10 | — | 10 | 10 | 9 | — | — | 0 | 8 | — | 0 | 2 | 0 | 3 |
| sec.-Butinyl-N-(3-(N,N-diethylcarbamoyloxy)-phenyl)-carbamate | 3 | — | — | 9 | 8 | 10 | — | — | 0 | 2 | 2 | 0 | 0 | 0 | 0 |
| sec.-Butinyl-N-(3-(N,N-bis-(2-chloroethyl)-carbamoyloxy)-phenyl)-carbamate | 3 | 10 | — | 10 | 9 | 10 | — | — | 0 | 6 | 7 | 0 | 1 | 0 | 0 |
| Isopropyl-N-(3-(N,N-bis-(1-chloro-1-methylethyl)-carbamoyloxy)-phenyl)-carbamate | 3 | 9 | 9 | 10 | 10 | 10 | — | — | 0 | 2 | 1 | 0 | 3 | 0 | 0 |
| Isopropyl-N-(3-(N-methyl-N-(2-bromoethyl)-carbamoyloxy)-phenyl)-carbamate | 3 | 10 | — | 10 | 10 | 10 | — | — | 1 | 8 | — | 8 | 6 | 0 | 8 |

| Agent of Invention | Ipomoea purpurea | Polygonum lapathifolium | Brassica oleracea | Beta vulgaris | Solanum lycopersicum | Allium sativum | Cucumis sativus | Medicago sativa | Helianthus annus | Lactuca capitata | Trifolium spp. | Spinaia oleracea | Setaria italica |
|---|---|---|---|---|---|---|---|---|---|---|---|---|---|
| sec.-Butinyl-N-(3-(N-methyl-N-phenyl-carbamoyloxy)-phenyl)-carbamate | 0 | 1 | 0 | 0 | 0 | 4 | 0 | 0 | 0 | — | — | — | 0 |
| sec.-Butinyl-N-(3-(N-ethyl-N-ethyl-N-phenyl-carbamoyloxy)-phenyl)-carbamate | 0 | 0 | 0 | 2 | 1 | 8 | 0 | 1 | 0 | — | — | — | 2 |
| sec.-Butinyl-N-(3-(N,N-diethyl-carbamoyloxy)-phenyl)-carbamate | 0 | 0 | 0 | 0 | 1 | 0 | 0 | 0 | 0 | — | — | — | 0 |
| sec.-Butinyl-N-(3-(N,N-bis-(2-chloroethyl)-carbamoyloxy)-phenyl)-carbamate | 0 | 1 | 0 | 0 | 0 | 0 | 0 | 0 | 0 | — | — | — | 1 |
| Isopropyl-N-(3-N,N-bis-(1-chloro-1-methylethyl)-carbamoyloxy)-phenyl)-carbamate | 3 | 0 | 6 | 1 | 0 | 1 | 0 | 0 | 0 | — | — | — | 3 |
| Isopropyl-N-(3-(N-methyl-N-(2-bromoethyl)-carbamoyloxy)-phenyl)-carbamate | 7 | 4 | 8 | — | 8 | — | 0 | 0 | 7 | — | — | — | 3 |

| Agent of Invention | kg/ha active substance | Cotton | Soybean | Corn | Wheat | Barley | Rye | Oats | Stellaria media | Senecio vulgaris | Matricaria chamomilla | Lamium amplexicaule | Centaurea cyanus | Amaranthus retroflexus | Chrysanthemum segetum |
|---|---|---|---|---|---|---|---|---|---|---|---|---|---|---|---|
| sec.-Butyl-N-(3-N,benzyl-N-methylcarbamoyloxy)-phenyl)-carbamate | 3 | 0 | — | 10 | 10 | 10 | — | — | 0 | 1 | 8 | 0 | 3 | 0 | 0 |
| sec.-Butyl-N-(3-(N-ethyl-N-(3-methylphenyl)-carbamoyloxy)-phenyl)-carbamate | 3 | — | — | 10 | 10 | 10 | — | — | 0 | 0 | 0 | 0 | 0 | 0 | 0 |
| sec.-Butyl-N-(3-(N,N-diallylcarbamoyloxy)-phenyl)-carbamate | 3 | — | — | 10 | 9 | 9 | — | — | 0 | 0 | 0 | 0 | 0 | 0 | 0 |
| Allyl-N-(3-(N-butyl-N-phenylcarbamoyloxy)-phenyl)-carbamate | 3 | 10 | — | 10 | 10 | 10 | — | — | 0 | 0 | 0 | 0 | 0 | 0 | 0 |
| Allyl-n-(3-(N-ethyl-N-(2-chloroethyl)-carbamoyloxy)-phenyl)-carbamate | 3 | 10 | — | 10 | 10 | 9 | — | — | 0 | — | — | 0 | 0 | 0 | 8 |
| sec.-Butyl-N-(3-(N,N-bis-(1-chloro-1-methylethyl)-carbamoyloxy)-phenyl)-carbamate | 3 | — | 8 | 10 | 10 | 10 | — | — | 0 | 0 | 2 | 0 | 0 | 0 | 0 |

-continued

| Agent of Invention | Ipomoea purpurea | Polygonumla pathifolium | Brassica oleracea | Beta vulgaris | Solanum lycopersicum | Allium sativum | Cucumis sativus | Medicago sativa | Helianthus annus | Lactuca capitata | Trifolium spp. | Spinaia oleracea | Setaria italica |
|---|---|---|---|---|---|---|---|---|---|---|---|---|---|
| sec.-Butyl-N-(3-(N-benzyl-N-methyl-carbamoyloxy)-phenyl)-carbamate | 0 | 0 | 0 | 0 | 1 | 5 | 0 | 1 | 0 | — | — | — | 1 |
| sec.-Butyl-N-(3-(N-ethyl-N-(3-methyl-phenyl)-carbamoyloxy)-phenyl)-carbamate | 0 | 0 | 0 | 0 | 0 | 0 | 0 | 0 | 0 | — | — | — | 0 |
| sec.-Butyl-N-(3-(N,N-diallylcarbamoyloxy)-phenyl)-carbamate | 0 | 0 | 0 | 0 | 0 | 0 | 0 | 0 | 0 | — | — | — | 0 |
| Allyl-N-(3-(N-butyl-N-phenyl-carbamoyloxy)-phenyl)-carbamate | 0 | 0 | 0 | 0 | 0 | 0 | 0 | 0 | 0 | — | — | — | 0 |
| Allyl-N-(3-(N-ethyl-N-(2-chloroethyl)-carbamoyloxy)-phenyl)-carbamate | 0 | 0 | 0 | 0 | 0 | 4 | 0 | 0 | 0 | — | — | — | 0 |
| sec.-Butyl-N-(3-(N,N-bis-(1-chloro-1-methylethyl)-carbamoyloxy)-phenyl)-carbamate | 5 | 0 | 4 | 0 | 0 | 0 | 0 | 0 | 0 | — | — | — | 3 |

| Agent of Invention | kg/ha active substance | Cotton | Soybean | Corn | Wheat | Barley | Rye | Oats | Stellaria media | Senecio vulgaris | Matricaria chamomilla | Lamium amplexicaule | Centaurea cyanus | Amaranthus retroflexus | Chrysanthemum segetum |
|---|---|---|---|---|---|---|---|---|---|---|---|---|---|---|---|
| Allyl-N-(3-(N-ethyl-N-butylcarbamoyloxy)-phenyl)-carbamate | 3 | 10 | — | 10 | 10 | 10 | — | — | 0 | 7 | — | 0 | 4 | 0 | 4 |
| Allyl-N-(3-(N-ethyl-N-phenylcarbamoyloxy)-phenyl)-carbamate | 3 | 8 | — | 10 | 10 | 10 | — | — | 0 | 0 | 1 | 0 | 0 | 0 | 0 |
| Allyl-N-(3-(N,N-bis-(1-chloro-1-methylethyl)-carbamoyloxy)-phenyl)-carbamate | 3 | 10 | — | 10 | 10 | 10 | — | — | 0 | 1 | 6 | 0 | 0 | 0 | 0 |
| Isopropyl-N-(3-(N-(2-chlorpropyl)-N-cyclohexyl-carbamoyloxy)-phenyl)-carbamate | 3 | 10 | — | — | 10 | 10 | — | — | 1 | 0 | 0 | 0 | 1 | 3 | 0 |
| Isopropyl-N-(3-(N-(4-methyl)-N-propylcarbamoyloxy)-phenyl)-carbamate | 3 | 10 | — | 10 | 10 | 10 | — | — | 0 | 0 | 0 | 1 | 0 | 0 | 0 |
| Isopropyl-N-(3-(N-(4-ethylphenyl)-N-propylcarbamoyloxy)-phenyl)-carbamate | 3 | 10 | — | 10 | 10 | 10 | — | — | 0 | 0 | 0 | 1 | 0 | 0 | 0 |

| Agent of Invention | Ipomoea purpurea | Polygonumla pathifolium | Brassica oleracea | Beta vulgaris | Solanum lycopersicum | Allium sativum | Cucumis sativus | Medicago sativa | Helianthus annus | Lactuca capitata | Trifolium spp. | Spinaia oleracea | Setaria italica |
|---|---|---|---|---|---|---|---|---|---|---|---|---|---|
| Allyl-N-(3-(N-ethyl-N-butyl-carbamoyloxy)-phenyl)-carbamate | 2 | 1 | 1 | 0 | 0 | 0 | 0 | 0 | 0 | — | — | — | 2 |
| Allyl-N-(3-(N-ethyl-N-phenyl-carbamoyloxy)-phenyl)-carbamate | 0 | 0 | 0 | 0 | 0 | 0 | 0 | 0 | 0 | — | — | — | 0 |
| Allyl-N-(3-(N,N-bis-(1-chloro-1-methylethyl)-carbamoyloxy)-phenyl)-carbamate | 3 | 0 | 3 | 0 | 0 | 3 | 0 | 1 | 0 | — | — | — | 3 |
| Isopropyl-N-(3-(N-(2-chlorpropyl)-N-cyclohexyl-carbamoyloxy)-phenyl)-carbamate | 8 | 0 | 8 | 2 | 3 | 2 | 1 | 5 | 0 | — | — | — | 3 |
| Isopropyl-N-(3-(N-(4-methyl)-N-propyl-carbamoyloxy)-phenyl)-carbamate | 5 | 0 | 3 | 0 | 3 | 0 | 0 | 1 | 0 | — | — | — | 0 |
| Isopropyl-N-(3-(N-(4-ethylphenyl)-N-propylcarbamoyloxy)-phenyl)-carbamate | 5 | 0 | 3 | 0 | 1 | 5 | 0 | 4 | 0 | — | — | — | 4 |

| Agent of Invention | kg/ha active substance | Cotton | Soybean | Corn | Wheat | Barley | Rye | Oats | Stellaria media | Senecio vulgaris | Matricaria chamomilla | Lamium amplexicaule | Centaurea cyanus | Amaranthus retroflexus | Chrysanthemum segetum |
|---|---|---|---|---|---|---|---|---|---|---|---|---|---|---|---|
| sec.-Butyl-N-(3-(N,N-di-sec.-butylcarbamoyloxy)-phenyl)-carbamate | 3 | 7 | 8 | 10 | 10 | 9 | — | — | — | — | 3 | — | — | — | 5 |
| Allyl-N-(3-(N,N-dibutyl-carbamoyloxy)-phenyl)- | 3 | 7 | — | 8 | 10 | 9 | — | — | 1 | 3 | 0 | 0 | 3 | 0 | 1 |

-continued

| Agent of Invention | | | | | | | | | | | | | | |
|---|---|---|---|---|---|---|---|---|---|---|---|---|---|---|
| carbamate 1-Methylpropinyl-N-(3-(N-phenyl-N-isopropyl-carbamoyloxy)-phenyl)-carbamate | 3 | — | — | 9 | 9 | 9 | — | — | 0 | 3 | 0 | 0 | 1 | 0 | 1 |
| Allyl-N-(3-(N-phenyl-N-isopropylcarbamoyloxy)-phenyl)-carbamate | 3 | 10 | — | 9 | 9 | 9 | — | — | 0 | 1 | 0 | 0 | 0 | 0 | 0 |
| 1-Methyl-N-(3-(N-phenyl-N-propylcarbamoyloxy)-phenyl)-carbamate | 3 | — | — | 9 | 10 | 9 | — | — | 0 | 0 | 0 | 0 | 0 | 0 | 0 |
| Allyl-N-(3-(N-phenyl-N-propylcarbamoyloxy)-phenyl)-carbamate | 3 | — | — | 10 | 10 | 10 | — | — | 0 | 0 | 0 | 0 | 0 | 0 | 0 |

| Agent of Invention | Ipomoea purpurea | Polygonum lapathifolium | Brassica oleracea | Beta vulgaris | Solanum lycopersicum | Allium sativum | Cucumis sativus | Medicago sativa | Helianthus annus | Lactuca capitata | Trifolium spp. | Spinaia oleracea | Setaria italica |
|---|---|---|---|---|---|---|---|---|---|---|---|---|---|
| sec.-Butyl-N-(3-(N,N-di-sec.-butyl-carbamoyloxy)-phenyl)-carbamate | — | 2 | 5 | 7 | — | — | 2 | — | — | — | — | — | — |
| Allyl-N-(3-(N,N-dibutylcarbamoyloxy)-phenyl)-carbamate | 5 | 0 | 0 | 0 | 1 | 6 | 0 | 1 | 0 | — | — | — | 4 |
| 1-Methylpropinyl-N-(3-(N-phenyl-N-isopropylcarbamoyloxy)-phenyl)-carbamate | 0 | 0 | 0 | 0 | 2 | 0 | 0 | 1 | 0 | — | — | — | 0 |
| Allyl-N-(3-(N-phenyl-N-isopropylcarbamoyloxy)-phenyl)-carbamate | 0 | 0 | 0 | 0 | 0 | 0 | 0 | 0 | 0 | — | — | — | 0 |
| 1-Methylpropinyl-N-(3-(N-phenyl-N-propyl-carbamoyloxy)-phenyl)-carbamate | 0 | 0 | 0 | 0 | 0 | 1 | 0 | 0 | 0 | — | — | — | 0 |
| Allyl-N-(3-(N-phenyl-N-propyl-carbamoyloxy)-phenyl)-carbamate | 0 | 0 | 0 | 0 | 0 | 0 | 0 | 0 | 0 | — | — | — | 0 |

| Agent of Invention | kg/ha active substance | Cotton | Soybean | Corn | Wheat | Barley | Rye | Oats | Stellaria media | Senecio vulgaris | Matricaria chamomilla | Lamium amplexicaule | Centaurea cyanus | Amaranthus retroflexus | Chrysanthemum segetum |
|---|---|---|---|---|---|---|---|---|---|---|---|---|---|---|---|
| Isopropyl-N-(3-(N-(2-bromoethyl)-N-butylcarbamoyloxy)-phenyl)-carbamate | 3 | 10 | 9 | 10 | 10 | 10 | — | — | 3 | 6 | 3 | 5 | 5 | 0 | 3 |
| 1-Methylpropinyl-N-(3-(N-ethyl-N-butyl-carbamoyloxy)-phenyl)-carbamate | 3 | 10 | 9 | 10 | 10 | 10 | — | — | 0 | — | — | 0 | — | 0 | 6 |
| sec.-Butyl-N-(3-(N-ethyl-N-(3-chlorophenyl)-carbamoyloxy)-phenyl)-carbamate | 3 | — | — | 10 | 10 | 10 | — | — | 0 | 0 | 0 | 1 | 0 | 0 | 0 |
| Isopropyl-N-(3-(N-ethyl-N-(3-chlorophenyl)-carbamoyloxy)-phenyl)-carbamate | 3 | 9 | — | — | 9 | — | — | — | 0 | 0 | 0 | 0 | 0 | 0 | 0 |
| sec.-Butyl-N-(3-(N-methyl-N-phenylcarbamoyloxy)-phenyl)-carbamate | 3 | — | — | 7 | 7 | 7 | — | — | 0 | 0 | 0 | 0 | 0 | 0 | 0 |
| Isopropyl-N-(3-(N,N-dibutylcarbamoyloxy)-phenyl)-carbamate | 3 | 8 | — | 10 | 10 | 10 | — | — | 0 | 8 | — | 0 | 3 | 0 | 0 |

| Agent of Invention | Ipomoea purpurea | Polygonum lapathifolium | Brassica oleracea | Beta vulgaris | Solanum lycopersicum | Allium sativum | Cucumis sativus | Medicago sativa | Helianthus annus | Lactuca capitata | Trifolium spp. | Spinaia oleracea | Setaria italica |
|---|---|---|---|---|---|---|---|---|---|---|---|---|---|
| Isopropyl-N-(3-(N-(2-bromoethyl)-N-butyl-carbamoyloxy)-phenyl)-carbamate | — | 2 | 3 | 0 | — | — | 3 | 1 | 1 | — | — | — | 5 |
| 1-Methylpropinyl-N-(3-(N-ethyl-N-butyl-carbamoyloxy)-phenyl)-carbamate | 7 | 0 | 3 | 2 | — | — | 2 | 2 | 6 | — | — | — | — |
| sec.-Butyl-N-(3-(N-ethyl-N-(3-chloro-phenyl)-carbamoyloxy)-phenyl)-carbamate | 0 | 1 | 0 | 0 | 3 | 3 | 0 | 2 | 0 | — | — | — | 5 |
| Isopropyl-N-(3-(N-ethyl-N-(3-chloro-phenyl)-carbamoyloxy)-phenyl)-carbamate | 0 | 0 | 0 | 0 | 0 | 0 | 0 | 0 | 0 | — | — | — | 0 |
| sec.-Butyl-N-(3-(N-methyl-N-phenyl- | | | | | | | | | | | | | |

-continued

| | | | | | | | | | | | | | |
|---|---|---|---|---|---|---|---|---|---|---|---|---|---|
| carbamoyloxy)-phenyl)-carbamate | 0 | 0 | 0 | 0 | 0 | 0 | 0 | 0 | 0 | — | — | — | 0 |
| Isopropyl-N-(3-(N,N-dibutylcarbamoyl-oxy)-phenyl)-carbamate | 0 | 6 | 0 | 0 | 1 | 6 | 0 | 0 | 0 | — | — | — | 2 |

| Agent of Invention | kg/ha active sub-stance | Cot-ton | Soy-bean | Corn | Wheat | Bar-ley | Rye | Oats | Stel-laria me-dia | Se-necio vul-garis | Ma-tri-car-ia cha-mom-illa | La-mium am-plexi-caule | Cen-taurea cyanus | Ama-ran-thus re-tro-flex-us | Chrys-anthe-mum se-getum |
|---|---|---|---|---|---|---|---|---|---|---|---|---|---|---|---|
| Isopropyl-N-(3-(N-butyl-N-(2-chloroethyl)-carba-moyloxy)-phenyl)-car-bamate | 3 | 10 | 8 | 10 | 10 | 10 | — | — | 7 | 7 | 8 | — | 0 | 5 | 0 |
| Methyl-N-(3-(ethyl-N-(3-chlorophenyl)-carba-moyloxy)-phenyl)-car-bamate | 3 | — | — | 10 | 10 | 8 | — | — | 0 | 0 | 0 | 0 | 0 | 0 | 0 |
| Methyl-N-(3-(N-methyl-N-(3,4-dichlorophenyl)-carbamoyloxy)-phenyl)-carbamate | 3 | — | — | 8 | — | — | — | — | 0 | 0 | 0 | 0 | 0 | 0 | 0 |
| Ethyl-N-(3-(N-ethyl-N-(3-chlorophenyl)-carba-moyloxy)-phenyl)-car-bamate | 3 | 9 | — | 10 | 10 | 10 | — | — | 2 | 3 | 1 | 0 | 0 | 0 | 1 |
| Isopropyl-N-(3-(N-cy-clohexyl-N-(2-chloro-ethyl)-carbamoyloxy)-phenyl)-carbamate | 3 | 10 | — | 9 | 8 | 9 | — | — | 0 | 4 | 0 | 0 | 0 | 0 | 0 |

| Agent of Invention | Ipo-moea pur-purea | Poly-go-num la pathi-folium | Bras-sica oler-acea | Beta vul-garis | Sola-num lyco-persi-cum | Al-lium sati-vum | Cu-cu-mis sa-tivus | Me-di-cago sa-tiva | He-lian-thus an-nus | Lac-tuca ca-pi tata | Tri-fo-lium spp. | Spi-naia oler-acea | Se-taria ital-ica |
|---|---|---|---|---|---|---|---|---|---|---|---|---|---|
| Isopropyl-N-(3-(N-butyl-N-(2-chloro-ethyl)-carbamoyloxy)-phenyl)-carbamate | — | — | 8 | — | — | — | 0 | 3 | 8 | — | — | — | 8 |
| Methyl-N-(3-(N-ethyl-N-(3-chlorophenyl)-carbamoyloxy)-phenyl)-carbamate | 0 | 0 | 0 | 0 | 0 | 0 | 0 | 0 | 0 | — | — | — | 0 |
| Methyl-N-(3-(N-methyl-N-(3,4-dichlor-phenyl)-carbamoyloxy)-phenyl)-carbamate | 0 | 0 | 0 | 0 | 0 | 0 | 0 | 0 | 0 | — | — | — | 0 |
| Ethyl-N-(3-(N-ethyl-N-(3-chlorophenyl)-carbamoyloxy)-phenyl)-carbamate | 7 | 0 | 3 | 0 | 5 | 1 | 0 | 1 | 0 | — | — | — | — |
| Isopropyl-N-(3-(N-cyclohexyl-N-(2-chlorethyl)-carbamoyloxy)-phenyl)-carbamate | 8 | 0 | 1 | 0 | 4 | 0 | 0 | 2 | 0 | — | — | — | 3 |

| Agent of Invention | kg/ha active sub-stance | Cot-ton | Soy-bean | Corn | Wheat | Bar-ley | Rye | Oats | Stel-laria me-dia | Se-necio vul-garis | Ma-tri-car-ia cha-mom-illa | La-mium am-plexi-caule | Cen-taurea cyanus | Ama-ran-thus re-tro-flex-us | Chrys-anthe-mum se-getum |
|---|---|---|---|---|---|---|---|---|---|---|---|---|---|---|---|
| sec.-Butyl-N-(3-(N-methyl-N-(1-methylpro-pinyl)-carbamoyl-oxy)-phenyl)-carbamate | 3 | — | — | — | — | — | — | — | 0 | — | — | 0 | 2 | 0 | — |
| Propyl-N-(3-(N,N-dime-thylcarbamoyloxy)-phe-nyl)-carbamate | 3 | — | 8 | 10 | 10 | 10 | — | — | 2 | 5 | 5 | 4 | 4 | 5 | — |
| Propyl-N-(3-(N,N-dibu-tylcarbamoyloxy)-phe-nyl)-carbamate | 3 | 10 | — | 10 | 10 | 10 | — | — | 1 | 3 | 3 | 2 | 5 | 3 | 3 |
| Propyl-N-(3-(N,N-dipro-pylcarbamoyloxy)-phe-nyl)-carbamate | 3 | 10 | — | 8 | 10 | 8 | — | — | 0 | 5 | — | 0 | 3 | 0 | 4 |
| Isopropyl-N-(3-(N-me-thyl-N-(1-methyl-2-propi-nyl)-carbamoyloxy)-phe-nyl)-carbamate | 3 | 10 | 7 | 10 | 10 | 8 | — | — | 0 | — | — | 0 | 2 | 0 | — |

| Agent of Invention | Ipo-moea pur-purea | Poly-go-num la pathi-folium | Bras-sica oler-acea | Beta vul-garis | Sola-num lyco-persi-cum | Al-lium sati-vum | Cu-cu-mis sa-tivus | Me-di-cago sa-tiva | He-lian-thus an-nus | Lac-tuca ca-pi tata | Tri-fo-lium spp. | Spi-naia oler-acea | Se-taria ital-ica |
|---|---|---|---|---|---|---|---|---|---|---|---|---|---|
| sec.-Butyl-N-(3-(N-methyl-N-(1- | | | | | | | | | | | | | |

-continued

| | | | | | | | | | | | | | | |
|---|---|---|---|---|---|---|---|---|---|---|---|---|---|---|
| methyl-propinyl)-carbamoyloxy)-phenyl)-carbamate | 0 | 0 | — | — | — | — | — | — | — | — | — | — | — | 0 |
| Propyl-N-(3-(N,N-dimethylcarbamoyloxy)-phenyl)-carbamate | 2 | 5 | — | — | — | — | — | — | — | — | — | — | — | — |
| Propyl-N-(3-(N,N-dibutyl-carbamoyloxy)-phenyl)-carbamate | 3 | 1 | — | — | — | — | — | — | — | — | — | — | — | 5 |
| Propyl-N-(3-(N,N-dipropylcarbamoyloxy)-phenyl)-carbamate | 1 | 0 | — | — | — | — | — | — | — | — | — | — | — | 0 |
| Isopropyl-N-(3-(N-methyl-N-(1-methyl-2-propinyl)-carbamoyloxy)-phenyl)-carbamate | 1 | 0 | — | — | — | — | — | — | — | — | — | — | — | 0 |

| Agent of Invention | kg/ha active substance | Cotton | Soybean | Corn | Wheat | Barley | Rye | Oats | Stellaria media | Senecio vulgaris | Matricaria chamomilla | Lamium amplexicaule | Centaurea cyanus | Amaranthus retroflexus | Chrysanthemum segetum |
|---|---|---|---|---|---|---|---|---|---|---|---|---|---|---|---|
| Propyl-N-(3-(N-ethyl-N-(3-methylphenyl)-carbamoyloxy)-phenyl)-carbamate | 3 | — | — | 5 | 10 | 8 | — | — | 0 | 0 | 0 | 0 | 0 | 0 | 0 |
| Propyl-N-(3-(N-ethyl-N-(4-methylphenyl)-carbamoyloxy)-phenyl)-carbamate | 3 | — | — | 8 | 10 | 5 | — | — | 0 | 0 | 0 | 0 | 0 | 0 | 0 |
| Propyl-N-(3-(N-ethyl-N-butylcarbamoyloxy)-phenyl)-carbamate | 3 | — | — | 10 | 7 | — | — | — | 0 | 1 | 0 | 0 | 0 | 0 | 0 |
| Isopropyl-N-(3-(N-isopropyl-N-(2-chloroethyl)-carbamoyloxy)-phenyl)-carbamate | 3 | 10 | — | — | 5 | — | — | — | 0 | 2 | 1 | 0 | 1 | 0 | 1 |
| Propyl-N-(3-(N-di-sec.-butylcarbamoyloxy)-phenyl)-carbamate | 3 | 10 | 8 | 10 | 10 | 10 | — | — | 1 | — | — | 0 | — | 0 | 1 |
| Isopropyl-N-(3-(N-tert.-butyl-N-2-chloroethylcarbamoyloxy)-phenyl)-carbamate | 3 | 10 | — | 10 | 10 | 10 | — | — | 0 | — | — | 1 | 5 | 3 | 0 |

| Agent of Invention | Ipomoea purpurea | Polygonum lapathifolium | Brassica oleracea | Beta vulgaris | Solanum lycopersicum | Allium sativum | Cucumis sativus | Medicago sativa | Helianthus annus | Lactuca capitata | Trifolium spp. | Spinaia oleracea | Setaria italica |
|---|---|---|---|---|---|---|---|---|---|---|---|---|---|
| Propyl-N-(3-(N-ethyl-N-(3-methylphenyl)-carbamoyloxy)-phenyl)-carbamate | 1 | 0 | — | — | — | — | — | — | — | — | — | — | 0 |
| Propyl-N-(3-(N-ethyl-N-(4-methylphenyl)-carbamoyloxy)-phenyl)-carbamate | 0 | 0 | — | — | — | — | — | — | — | — | — | — | 0 |
| Propyl-N-(3-(N-ethyl-N-butyl-carbamoyloxy)-phenyl)-carbamate | 0 | 0 | — | — | — | — | — | — | — | — | — | — | 0 |
| Isopropyl-N-(3-(N-isopropyl-N-(2-chloroethyl)-carbamoyloxy)-phenyl)-carbamate | | 0 | — | — | — | | | | | | | | |
| Propyl-N-(3-(N-di-sec.-butyl-carbamoyloxy)-phenyl)-carbamate | 3 | 1 | — | — | — | — | — | — | — | — | — | — | 5 |
| Isopropyl-N-(3-(N-tert.-butyl-N-2-chloroethylcarbamoyloxy)-phenyl)-carbamate | 0 | 0 | — | — | — | — | — | — | — | — | — | — | 3 |

| Agent of Invention | kg/ha active substance | Cotton | Soybean | Corn | Wheat | Barley | Rye | Oats | Stellaria media | Senecio vulgaris | Matricaria chamomilla | Lamium amplexicaule | Centaurea cyanus | Amaranthus retroflexus | Chrysanthemum segetum |
|---|---|---|---|---|---|---|---|---|---|---|---|---|---|---|---|
| 3-Chlorpropyl-N-(3-(N-phenyl-N-propyl-carbamoyloxy)-phenyl)-carbamate | 3 | — | — | 10 | 9 | 9 | — | — | 0 | 0 | 0 | 0 | 0 | 0 | 0 |
| sec.-Butyl-N-(3-(N,N-di-isobutylcarbamoyloxy)-phenyl)-carbamate | 3 | 10 | — | 10 | 10 | 10 | — | — | 0 | 2 | 2 | 1 | 1 | 0 | 0 |
| sec.-Butyl-N-(3-(N,N-bis-(2-bromoethyl)-carbamoyloxy)-phenyl)-carbamate | 3 | — | — | 10 | 10 | 10 | — | — | 1 | 0 | 3 | 1 | 0 | 0 | 0 |
| 2-Bromoethyl-N-(3-(N- | | | | | | | | | | | | | | | |

| Agent of Invention | | | | | | | | | | | | | | |
|---|---|---|---|---|---|---|---|---|---|---|---|---|---|---|
| phenyl-N-phenyl-propyl-carbamoyloxy)-phenyl)-carbamate | 3 | — | — | 10 | 10 | 10 | — | — | 1 | 1 | 3 | 0 | 1 | 0 | 0 |
| 2-Chloroethyl-N-(3-(N-phenyl-N-propylcarbamoyloxy)-phenyl)-carbamate | 3 | 8 | — | 10 | 10 | 10 | — | — | 0 | 4 | — | 0 | 3 | 0 | 1 |
| Isopropyl-N-(3-phenyl-N-propylcarbamoyloxy)-phenyl)-carbamate | 3 | 10 | — | — | 8 | — | — | — | 0 | 0 | 0 | 0 | 0 | 0 | 0 |

| Agent of Invention | Ipomoea purpurea | Polygonum pathifolium | Brassica oleracea | Beta vulgaris | Solanum lycopersicum | Allium sativum | Cucumis sativus | Medicago sativa | Helianthus annus | Lactuca capi tata | Trifolium spp. | Spinaia oleracea | Setaria italica |
|---|---|---|---|---|---|---|---|---|---|---|---|---|---|
| 3-Chlorpropyl-N-(3-(N-phenyl-N-propyl-carbamoyloxy)-phenyl)-carbamate | 0 | 0 | — | — | — | — | — | — | — | — | — | — | 0 |
| sec.-Butyl-N-(3-(N,N-diisobutyl-carbamoyloxy)-phenyl)-carbamate | 2 | 0 | — | — | — | — | — | — | — | — | — | — | — |
| sec.-Butyl-N-(3-(N,N-bis-(2-bromo-ethyl)-carbamoyloxy)-phenyl-carbamate | — | 1 | — | — | — | — | — | — | — | — | — | — | 3 |
| 2-Bromoethyl-N-(N-phenyl-N-phenyl-propyl-carbamoyloxy)-phenyl)-carbamate | 2 | 0 | — | — | — | — | — | — | — | — | — | — | 1 |
| 2-Chloroethyl-N-(3-(N-phenyl-N-propyl-carbamoyloxy)-phenyl)-carbamate | 0 | 0 | — | — | — | — | — | — | — | — | — | — | 2 |
| Isopropyl-N-(3-(N-phenyl-N-propyl-carbamoyloxy)-phenyl)-carbamate | 0 | 0 | — | — | — | — | — | — | — | — | — | — | 0 |

| Agent of Invention | kg/ha active substance | Cotton | Soybean | Corn | Wheat | Barley | Rye | Oats | Stellaria media | Senecio vulgaris | Matricaria chamomilla | Lamium amplexicaule | Centaurea cyanus | Amaranthus retroflexus | Chrysanthemum segetum |
|---|---|---|---|---|---|---|---|---|---|---|---|---|---|---|---|
| Propyl-N-(3-(N-phenyl-N-propylcarbamoyloxy)-phenyl)-carbamate | 3 | — | — | — | 8 | — | — | — | 0 | 0 | 0 | 0 | 0 | 0 | 0 |
| 2-Chloro-1-methylethyl-N-(3-(N-ethyl-N-(2-bromoethyl)-carbamoyloxy)-phenyl)-carbamate | 2 | 10 | 6 | 8 | 10 | 10 | — | — | 1 | — | — | 0 | 5 | 0 | 5 |
| sec.-Butyl-N-(3-(N-phenyl-N-propyl-carbamoyloxy)-phenyl)-carbamate | 3 | — | — | 10 | 10 | 10 | — | — | 0 | 0 | 0 | 0 | 0 | 0 | 0 |
| 2-Chloro-1-methylethyl-N-(3-N-phenyl-N-propylcarbamoyloxy)-phenyl)-carbamate | 3 | — | — | 10 | 10 | 10 | — | — | 0 | 0 | 0 | 0 | 0 | 0 | 0 |
| sec.-Butyl-N-(3-(N,N-dibutylcarbamoyloxy)-phenyl)-carbamate | 3 | — | — | 8 | 10 | 10 | — | — | 0 | 0 | 0 | 0 | 0 | 0 | 0 |
| sec.-Butyl-N-(3-(N-allyl-N-phenylcarbamoyloxy)-phenyl)-carbamate | 3 | — | — | 10 | 10 | 8 | — | — | 0 | 0 | 0 | 0 | 0 | 0 | 0 |

| Agent of Invention | Ipomoea purpurea | Polygonum pathifolium | Brassica oleracea | Beta vulgaris | Solanum lycopersicum | Allium sativum | Cucumis sativus | Medicago sativa | dia lianthus annus | Lactuca capi tata | Trifolium spp. | Spinaia oleracea | Setaria italica |
|---|---|---|---|---|---|---|---|---|---|---|---|---|---|
| Propyl-N-(3-(N-phenyl-N-propyl-carbamoyloxy)-phenyl)-carbamate | 0 | 0 | — | — | — | — | — | — | — | — | — | — | 0 |
| 2-chlor-1-methylethyl-N-(3-(N-ethyl-N-(2-bromoethyl)-carbamoyloxy)-phenyl)-carbamate | 2 | 1 | 0 | 0 | 0 | 0 | 0 | 0 | 0 | 0 | 0 | 0 | 0 |
| sec.-Butyl-N-(3-N-phenyl-N-propyl-carbamoyloxy)-phenyl)-carbamate | 0 | 0 | — | — | — | — | — | — | — | — | — | — | — |
| 2-Chlor-1-methylethyl-N-(3-(N-phenyl-N-propylcarbamoyloxy)-phenyl)-carbamate | 3 | 0 | — | — | — | — | — | — | — | — | — | — | 5 |
| sec.-Butyl-N-(3-N,N-dibutylcarbamoyloxy)-phenyl)-carbamate | 0 | 0 | — | — | — | — | — | — | — | — | — | — | 5 |
| sec.-Butyl-N-(3-(N-allyl-N-phenyl-carbamoyloxy)-phenyl)-carbamate | 0 | 0 | — | — | — | — | — | — | — | — | — | — | — |

-continued

| Agent of Invention | kg/ha active substance | Cotton | Soybean | Corn | Wheat | Barley | Rye | Oats | Stellaria media | Senecio vulgaris | Matricaria chamomilla | Lamium amplexicaule | Centaurea cyanus | Amaranthus retroflexus | Chrysanthemum segetum |
|---|---|---|---|---|---|---|---|---|---|---|---|---|---|---|---|
| 3-Chloropropyl-N-(3-(N-phenyl-N-allyl-carbamoyloxy)-phenyl)-carbamate | 3 | — | — | 10 | 10 | 10 | — | — | 0 | 0 | 0 | 0 | 0 | 0 | 0 |
| Isopropyl-N-(3-(N-isopropyl-N-(2-bromoethyl)-carbamoyloxy)-phenyl)-carbamate | 3 | 10 | — | 10 | 10 | 10 | — | — | 2 | — | 2 | 0 | 5 | 0 | — |
| Propyl-N-(3-(N,N-bis-2-bromoethyl)-carbamoyloxy)-phenyl)-carbamate | 3 | — | — | 10 | 7 | 8 | — | — | 2 | 0 | — | 2 | 0 | 0 | 0 |
| Propyl-N-(3-(N,N-diisobutyl-carbamoyloxy)-phenyl)-carbamate | 3 | — | — | 10 | 10 | 8 | — | — | 0 | 7 | — | 1 | 0 | 0 | 0 |
| Propyl-N-(3-(N,N-diethylcarbamoyloxy)-phenyl)-carbamate | 3 | — | — | 8 | 7 | 10 | — | — | 0 | — | — | 0 | 0 | 1 | — |
| 2-Chloro-1-methylethyl-N-(3-(N-methyl-n-phenylcarbamoyloxy)-phenyl)-carbamate | 3 | — | — | 8 | 8 | 10 | — | — | 0 | 0 | 0 | 0 | 2 | 0 | 0 |

| Agent of Invention | Ipomoea purpurea | Polygonum lapathifolium | Brassica oleracea | Beta vulgaris | Solanum lycopersicum | Allium sativum | Cucumis sativus | Medicago sativa | Helianthus annus | Lactuca capitata | Trifolium spp. | Spinaia oleracea | Setaria italica |
|---|---|---|---|---|---|---|---|---|---|---|---|---|---|
| 3-Chlorpropyl-N-(3-(N-phenyl-N-allyl-carbamoyloxy)-phenyl)-carbamate | 0 | 0 | — | — | — | — | — | — | — | — | — | — | 2 |
| Isopropyl-N-(3-(n-isopropyl-N-(2-bromoethyl)-carbamoyloxy)-phenyl)-carbamate | — | 0 | — | — | — | — | — | — | — | — | — | — | — |
| Propyl-N-(3-(N,N-bis-(2-bromoethyl)-carbamoyloxy)-phenyl)-carbamate | — | 7 | 0 | 0 | 6 | 0 | 0 | 0 | 0 | — | — | — | 0 |
| Propyl-N-(3-(N,N-diisobutyl-carbamoyloxy)-phenyl)-carbamate | 0 | 0 | 0 | 0 | 0 | 2 | 0 | 0 | 0 | — | — | — | 5 |
| Propyl-N-(3-(N,N-diethyl-carbamoyloxy)-phenyl)-carbamate | 0 | 0 | 0 | 0 | 0 | 3 | 0 | 0 | 0 | — | — | — | 0 |
| 2-Chlor-1-methylethyl-N-(3-(N-methyl-N-phenylcarbamoyloxy)-phenyl)-carbamate | 0 | 0 | 3 | 0 | 0 | 0 | 0 | — | 0 | — | — | — | 0 |

| Agent of Invention | kg/ha active substance | Cotton | Soybean | Corn | Wheat | Barley | Rye | Oats | Stellaria media | Senecio vulgaris | Matricaria chamomilla | Lamium amplexicaule | Centaurea cyanus | Amaranthus retroflexus | Chrysanthemum segetum |
|---|---|---|---|---|---|---|---|---|---|---|---|---|---|---|---|
| 2-Chloro-1-methylethyl-N-(3-(N,N-diethyl-carbamoyloxy)-phenyl)-carbamate | 3 | — | — | 10 | 10 | 10 | — | — | 1 | — | 0 | 0 | 3 | 0 | 2 |
| sec.-Butyl-N-(3-(N-tert.-butyl-N-(2-chloroethyl)-carbamoyloxy)-phenyl)-carbamate | 3 | — | 8 | 9 | 10 | 9 | — | — | 0 | 4 | 6 | 0 | 0 | 0 | 0 |
| sec.-Butyl-N-(3-(N-bromoethyl)-N-isopropyl-carbamoyloxy)-phenyl)-carbamate | 3 | — | 7 | 10 | 10 | 10 | — | — | 0 | 2 | 2 | 0 | 0 | 0 | 0 |
| Isopropyl-N-(3-methylphenyl)-N-propylcarbamoyloxy)-phenyl-carbamate | 3 | 10 | 7 | 10 | 9 | 9 | — | — | 0 | 0 | 1 | 0 | 0 | 0 | 0 |
| Isopropyl-N-(3-(N,N-diethylcarbamoyloxy)-phenyl)-carbamate | 3 | 10 | 8 | 10 | 10 | 10 | — | — | 0 | — | — | 0 | 1 | 0 | 0 |
| Isopropyl-N-(3-(N-(2-methylphenyl)-N-propylcarbamoyloxy)-phenyl-carbamate | 3 | 9 | — | 10 | 8 | 8 | — | — | 0 | — | — | 0 | 0 | 0 | 2 |

-continued

| Agent of Invention | Ipomoea purpurea | num la pathifolium | Brassica oleracea | Beta vulgaris | num lycopersicum | Allium sativum | cumis sativus | dicago sativa | lianthus annus | tuca capi tata | Trifolium spp. | Spinaia oleracea | Setaria italica |
|---|---|---|---|---|---|---|---|---|---|---|---|---|---|
| 2-Chlor-1-methylethyl-N-(3-(N,N-diethyl-carbamoyloxy)-phenyl)-carbamate | 0 | 0 | 0 | 0 | 0 | 5 | 0 | 0 | 1 | — | — | — | — |
| sec.-Butyl-N-(3-(N-tert.-butyl-N-(2-chloroethyl)-carbamoyloxy)-phenyl)-carbamate | 0 | 0 | 0 | 0 | 2 | 2 | 0 | 0 | 0 | — | — | — | 1 |
| sec.-Butyl-N-(3-(N-(2-bromoethyl)-N-isopropyl-carbamoyloxy)-phenyl)-carbamate | 0 | 0 | 0 | 0 | 0 | 1 | 0 | 0 | 0 | — | — | — | 5 |
| Isopropyl-N-(3-(N-(3-methylphenyl)-N-propylcarbamoyloxy)-phenyl)-carbamate | 0 | 0 | 2 | 0 | 1 | 0 | 0 | 0 | 0 | — | — | — | 0 |
| Isopropyl-N-(3-(N,N-diethyl-carbamoyloxy)-phenyl)-carbamate | 1 | 6 | 1 | 0 | 2 | 0 | 0 | 2 | 0 | — | — | — | 0 |
| Isopropyl-N-(3-(N-2-methylphenyl)-N-propylcarbamoyloxy)-phenyl)-carbamate | 0 | 0 | 0 | 0 | 0 | — | 0 | 0 | 0 | — | — | — | 0 |

| Agent of Invention | kg/ha active substance | Cotton | Soybean | Corn | Wheat | Barley | Rye | Oats | Stellaria media | Senecio vulgaris | Matricaria chamomilla | Lamium amplexicaule | Centaurea cyanus | Amaranthus retroflexus | Chrysanthemum segetum |
|---|---|---|---|---|---|---|---|---|---|---|---|---|---|---|---|
| Isopropyl-N-(3-(N-(3-methoxyphenyl)N-butyl-carbamoyloxy)-phenyl)-carbamate | 3 | 10 | 9 | 10 | 10 | 10 | — | — | 1 | — | — | 1 | 1 | 0 | 0 |
| Isopropyl-N-(3-(N-isobutyl-N-methylcarbamoyloxy)-phenyl)carbamate | 3 | 10 | — | 10 | 10 | 10 | — | — | 0 | — | — | 0 | 2 | 0 | 0 |
| sec.-Butyl-n-(3-(N-(4-ethylphenyl)-N-methyl-carbamoyloxy)-phenyl)-carbamoyloxy)-phenyl)-carbamate | 3 | — | 7 | 9 | 10 | 10 | — | — | 0 | 0 | 0 | 0 | 0 | 0 | 0 |
| sec.-Butyl-N-(3-(N-isopropyl-N-(2-chloroethyl)-carbamoyloxy)-phenyl)-carbamate | 3 | — | — | 9 | 10 | 10 | — | — | 0 | 1 | 4 | 0 | 0 | 1 | 0 |
| sec.-Butyl-N-(3-(N-2-phenylethyl)N-methyl carbamoyloxy)-phenyl)-carbamate | 3 | 7 | 7 | 10 | 10 | 10 | — | — | 0 | 2 | 2 | 0 | 2 | — | 1 |
| sec.-Butyl-N-(3-(N-ethyl-N-(4-methylphenyl)-carbamoyloxy)-phenyl)-carbamate | 3 | — | — | 10 | 10 | 9 | — | — | 0 | 0 | 0 | 0 | 0 | 0 | 0 |

| Agent of Invention | Ipomoea purpurea | Polygonum la pathifolium | Brassica oleracea | Beta vulgaris | Solanum lycopersicum | Allium sativum | Cucumis sativus | Medicago sativa | Helianthus annus | Lactuca capi tata | Trifolium spp. | Spinaia oleracea | Setaria italica |
|---|---|---|---|---|---|---|---|---|---|---|---|---|---|
| Isopropyl-N-(3-(n-3-methoxyphenyl)-N-butyl-carbamoyloxy)-phenyl)-carbamate | 3 | 5 | 1 | 0 | — | 5 | — | 2 | 0 | — | — | — | 2 |
| Isopropyl-N-(3-(n-isobutyl-N-methyl-carbamoyloxy)-phenyl)-carbamate | 1 | 0 | 0 | 0 | 0 | — | 0 | 0 | 0 | — | — | — | 1 |
| sec.-Butyl-N-(3-(N-(4-ethylphenyl)-N-methyl-carbamoyloxy)-phenyl)-carbamate | 0 | 0 | 0 | 0 | 3 | 0 | 0 | 0 | 0 | — | — | — | 1 |
| sec.-Butyl-N-(3-(N-isopropyl-N(2-chloroethyl)-carbamoyloxy)-phenyl)-carbamate | 1 | 0 | 0 | 0 | 1 | 0 | 0 | 0 | 0 | — | — | — | 1 |
| sec.-Butyl-N-(3-(N-(2-phenylethyl)-N-methyl-carbamoyloxy)-phenyl)-carbamate | 0 | 0 | 0 | 0 | 4 | 4 | 0 | 0 | 0 | — | — | — | 4 |
| sec.-Butyl-N-(3-(n-ethyl-N-(4-methylphenyl)-carbamoyloxy)-phenyl)-carbamate | 0 | 0 | 0 | 0 | 2 | 0 | 0 | 0 | 0 | — | — | — | 0 |

| Agent of Invention | kg/ha active substance | Cotton | Soybean | Corn | Wheat | Barley | Rye | Oats | Stellaria media | Senecio vulgaris | Matricaria chamomilla | Lamium amplexicaule | Centaurea cyanus | Amaranthus retroflexus | Chrysanthemum segetum |
|---|---|---|---|---|---|---|---|---|---|---|---|---|---|---|---|
| sec.-Butyl-N-(3-(N-ethyl | | | | | | | | | | | | | | | |

-continued

| Agent of Invention | | | | | | | | | | | | | | | |
|---|---|---|---|---|---|---|---|---|---|---|---|---|---|---|---|
| N-(2-bromoethyl)-carbamoyloxy)-phenyl)-carbamate | 3 | 3 | — | 10 | 10 | 10 | 10 | 10 | 5 | 4 | — | 0 | 1 | 0 | 0 |
| Isopropyl-N-(3-(N-ethyl-N-(2-bromoethyl)-carbamoyloxy)-phenyl)-phenyl)-carbamate | 3 | 10 | — | 10 | 10 | 10 | 10 | 10 | 2 | 4 | — | 0 | 1 | 0 | 0 |
| 2-Bromoethyl-N-(3-N-ethyl-N-phenylcarbamoyloxy)-phenyl)-carbamate | 3 | 10 | 9 | 10 | 10 | 10 | 10 | 10 | — | — | — | 2 | — | 1 | 4 |
| 2-Bromoethyl-N-(3-)N-butyl-N-phenylcarbamoyloxy)-phenyl)-carbamate | 3 | 10 | — | 10 | 10 | 10 | 10 | 10 | 2 | 2 | — | 0 | 0 | 0 | 1 |
| 2-Bromoethyl-N-(3-(N,-N-bis-(2-chloroethyl)-carbamoyloxy)-phenyl)-carbamate | 3 | 8 | — | 9 | 10 | 10 | 10 | 10 | 1 | 1 | 6 | 0 | 1 | 4 | 0 |
| Comparison Agents | | | | | | | | | | | | | | | |
| N-(3-Trifluoromethylphenyl)-N'nN'-dimethyl urea | 1 | 5 | 0 | 5 | 4 | 2 | 2 | 2 | 0 | 0 | 0 | 0 | 0 | 0 | 0 |
| 3-Methoxycarbonylaminophenyl-N-(3-methylphenyl)-carbamate | 1 | 4 | 5 | 4 | 5 | 6 | 4 | 3 | 0 | 0 | 1 | 0 | 0 | 4 | 0 |

| Agent of Invention | Ipomoea purpurea | Polygonum lapathifolium | Brassica oleracea | Beta vulgaris | Solanum lycopersicum | Allium sativum | Cucumis sativus | Medicago sativa | Helianthus annus | Lactuca capitata | Trifolium spp. | Spinaia oleracea | Setaria italica |
|---|---|---|---|---|---|---|---|---|---|---|---|---|---|
| sec.-Butyl-N-(3-(N-ethyl-N-(2-bromoethyl)-carbamoyloxy)-phenyl)-carbamate | 7 | 0 | 1 | 2 | 3 | 7 | 1 | 0 | 0 | 1 | 3 | 0 | 1 |
| Isopropyl-N-(3-N-ethyl-N-(2-bromoethyl)-carbomoyloxy)-phenyl)-carbamate | 5 | 1 | 1 | — | 5 | — | 0 | 1 | 0 | 1 | 6 | 0 | 1 |
| 2-Bromoethyl-N-(3-N-ethyl-N-phenyl-carbamoyloxy)-phenyl)-carbamate | — | 7 | 1 | — | — | — | 5 | 7 | — | — | — | 1 | 1 |
| 2-Bromoethyl-N-(3-(N-butyl-N-phenyl-carbamoyloxy)-phenyl)-carbamate | 1 | 0 | 0 | 0 | 0 | — | 0 | 1 | 0 | 1 | — | 1 | 3 |
| 2-Bromoethyl-N-(3-N,N-bis-(2-chloroethyl)-carbamoyloxy)-phenyl)carbamate | — | — | 0 | 0 | 0 | — | 0 | 0 | 4 | 0 | 0 | 0 | |
| Comparison Agent | | | | | | | | | | | | | |
| N-(3-Trifluoromethylphenyl)-N',N'-dimethyl-urea | 0 | 0 | 0 | 0 | 0 | 0 | 0 | 0 | 0 | 0 | 0 | 0 | 0 |
| 3-Methoxycarbonylaminophenyl-N-(3-methylphenyl)-carbamate | 0 | 0 | 4 | 7 | 0 | 0 | 0 | 0 | 1 | 2 | 0 | 0 | |

0 = total destruction;
10 = no damage

EXAMPLE 2

In the greenhouse, the malvaceous weeds Sida spinosa and Abutilon theophrasti were treated, the former in the foliage stage, the latter in the cotyledon stage, with the agents listed in the following table at an applied volume corresponding to 1 kg of active substance in 500 liters of aqueous emulsion per hectare, in the postemergence stage. After fourteen days the treatment was rated (0=total destruction, 10=no damage). The following compound was used as the known comparison agent.

3-Methoxycarbonylaminophenyl-N-(3'-methylphenyl)carbamate. The weeds were completely destroyed by the agents of the invention, while the comparison agent was almost ineffective.

| Agent of Invention | kg/ha | Sida spin. | Abutilon theo. |
|---|---|---|---|
| 1. Ethyl-N-(3-N-allyl-N-phenyl-carbamoyloxy)-phenyl)-carbamate | 1 | 2 | 0 |
| Ethyl-N-(3-(N-ethyl-N-phenyl-carbamoyloxy)-phenyl)-carbamate | 1 | 0 | 0 |
| 2. Isopropyl-N-(3-N-allyl-N-phenyl-carbamoyloxy)-phenyl)-carbamate | 1 | 0 | 0 |
| 3. Isopropyl-N-(3-ethyl-N-(2-chloroethyl)-carbamoyloxy)-phenyl)-carbamate | 1 | — | 0 |
| 4. Isopropyl-N-(3-(N,N-diisopropyl-carbamoyloxy)-phenyl)-carbamate | 1 | — | 0 |
| 5. Isopropyl-N-(3-(N-butyl-N-phenyl-carbamoyloxy)-phenyl)-carbamate | 1 | 0 | 0 |
| 6. Isopropyl-N-(3-N-ethyl-N-phenyl-carbamoyloxy)-phenyl)-carbamate | 1 | | |
| Comparison Agent | | | |
| 3-Methoxycarbonylaminophenyl-N-(3'-methylphenyl)-carbamate | 1 | 8 | 9 |
| Untreated control | 1 | 10 | 10 |

0 = total destruction;
10 = no damage

We claim:

1. The method for the control of weed growth in cotton fields which comprises treatment of said fields with a herbicidally effective amount of a composition comprising from about 20 to about 80 weight percent of a compound having the formula:

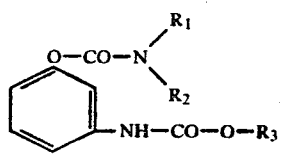

wherein $R_1$ is ethyl or allyl; $R_2$ is phenyl, alkylphenyl having from 1 to 3 carbons in the alkyl group, alkoxyphenyl having from 1 to 3 carbons in the alkoxy group, or halophenyl; and $R_3$ is methyl or ethyl at a rate sufficient to provide between about 0.5 and 5 kg of said compound per hectare.

* * * * *